(12) United States Patent
Maxwell et al.

(10) Patent No.: US 7,625,928 B2
(45) Date of Patent: Dec. 1, 2009

(54) NITROXIDE RADIOPROTECTOR FORMULATIONS AND METHODS OF USE

(75) Inventors: Kameron W. Maxwell, Rancho Santa Fe, CA (US); Peter C. Hoyle, Lovettsville, VA (US)

(73) Assignee: Mitos Pharmaceuticals, Inc., Newport Beach, CA (US)

( * ) Notice: Subject to any disclaimer, the term of this patent is extended or adjusted under 35 U.S.C. 154(b) by 1037 days.

(21) Appl. No.: 10/675,225

(22) Filed: Sep. 29, 2003

(65) Prior Publication Data

US 2005/0020633 A1 Jan. 27, 2005

Related U.S. Application Data

(60) Provisional application No. 60/429,887, filed on Nov. 26, 2002, provisional application No. 60/415,089, filed on Oct. 1, 2002.

(51) Int. Cl.
*A61K 31/445* (2006.01)
(52) U.S. Cl. .................................................... 514/327
(58) Field of Classification Search ...................... None
See application file for complete search history.

(56) References Cited

U.S. PATENT DOCUMENTS

| | | | |
|---|---|---|---|
| 5,352,442 A | 10/1994 | Proctor | |
| 5,462,946 A * | 10/1995 | Mitchell et al. | 514/315 |
| 5,840,734 A | 11/1998 | Bernstein | |
| 6,426,080 B1 * | 7/2002 | Golz-Berner et al. | 424/401 |

FOREIGN PATENT DOCUMENTS

| | | |
|---|---|---|
| EP | 0 327 263 A | 8/1989 |
| WO | WO 88/01163 A | 2/1988 |
| WO | WO 97/41826 | 11/1997 |
| WO | WO 00/78316 | 12/2000 |

OTHER PUBLICATIONS

Goffman, Thomas, et al. "Topical Application of Nitroxide Protects Radiation-Induced Alopecia in Guinea Pigs", International Journal of Radiation Oncology Biology Physics, 1992; vol. 22, No. 4; pp. 803-806.
Cuscela, Daniel, et al. "Protection from Radiation-Induced Alopecia with Topical Application of Nitroxides: Fractionated Studies", The Cancer Journal from Scientific American, 1996; vol. 2, No. 5, pp. 273-278.
Roberts, Dianna B., et al. "Acemannan-Containing Wound Dressing Gel Reduces Radiation-Induced Skin Reaction in C3H Mice", International Journal of Radiation Oncology Biology Physics, 1995; vol. 32, No. 4; pp. 1047-1052.
Yanagimoto, Go, et al. "Skin Disposition of Drugs After Topical Application in Hairless Rats", Biosciences Information Service ,1999; Abstract.
Supplementary European Search Report, Sep. 16, 2008.

* cited by examiner

*Primary Examiner*—Michael G. Hartley
*Assistant Examiner*—James W. Rogers
(74) *Attorney, Agent, or Firm*—Knobbe Martens Olson & Bear, LLP

(57) ABSTRACT

Pharmaceutical compositions useful in preventing and treating negative side effects accompanying radiotherapy are disclosed. More particularly, new formulations that can be applied to the skin and mucous membranes of patients undergoing radiotherapy and methods of using these formulations are disclosed.

23 Claims, 14 Drawing Sheets

US 7,625,928 B2

NITROXIDE RADIOPROTECTOR FORMULATIONS AND METHODS OF USE

RELATED APPLICATIONS

The present application claims priority to U.S. Provisional Application No. 60/415,089, filed Oct. 1, 2002, and U.S. Provisional Application No. 60/429,887, filed Nov. 26, 2002, both of which are expressly incorporated by reference in their entireties.

FIELD OF THE INVENTION

The present invention relates generally to the field of preventing or treating the negative side effects which accompany radiotherapy. More particularly, this invention relates to the discovery of new formulations that can be applied to the skin and mucous membranes of patients undergoing radiotherapy and methods of using these formulations.

BACKGROUND OF THE INVENTION

Radiation therapy is an important tool in the fight against cancer and is used in the treatment of as many as 50% of all cancer patients. Accordingly, more than half a million cancer patients receive radiation therapy each year. While the use of radiation therapy is an effective way to treat many kinds of cancer, there are many complications that may result. Common complications can include negative effects on the patients skin, hair follicles, and mucous membranes.

Common skin complications of radiotherapy include erythema and folliculitis. These disorders can be very irritating to patients as they both involve pruritus and redness of the skin. These and other skin complications can arise through oxidative and other stress caused by radiation. Other examples of skin conditions caused by radiation include fibrosis, dry desquamation and moist desquamation.

In addition, hair follicles are quite sensitive to radiotherapy. Accordingly, if hair is in the radiation treatment beam field, it can cease to grow and fall out. Losing one's hair can be a source of embarrassment and loss of self esteem.

Radiotherapy can also have negative effects on the mucous membranes in the eyes, nose, mouth, vagina, rectal mucosa and the like. For example, oral mucositis, also called stomatitis, results from the local effects of radiation to the oral mucosa. Mucositis is characterized by inflammation of the mucosa of the mouth and ranges from redness to severe ulceration. Symptoms of mucositis vary from pain and discomfort, to an inability to tolerate food or fluids. Even worse, oral mucositis may be so severe as to limit the patient's ability to tolerate further radiotherapy or chemotherapy.

Patients with damaged oral mucosa and a reduced immunity resulting from radiotherapy are also prone to opportunistic infections in the mouth. Accordingly, mucositis may also further compromise a patient's response to treatment and/or palliative care. It is therefore extremely important that mucositis be prevented whenever possible, or at least treated to reduce its severity and possible complications.

Another common mucous membrane condition caused by radiotherapy is proctitis. Proctitis is an inflammation of the lining of the rectum (rectal mucosa). The most common symptom is a frequent, or continuous sensation, or urge to have a bowel movement. Other symptoms include constipation, a feeling of rectal fullness, left-sided abdominal pain, passage of mucus through the rectum, rectal bleeding, and anorectal pain.

Some have previously suggested the use of Tempol, a stable nitroxide radical characterized by the chemical formula 4-hydroxy-2,2,6,6-tetramethylpiperidine-1-oxyl, as a topical formulation to ameliorate the effects of radiotherapy. (See e.g., Proctor, U.S. Pat. No. 5,352,442, and Mitchell, U.S. Pat. No. 5,462,946, both of which are hereby incorporated by reference in their entireties). These references limit the topical use of Tempol to formulations selected from creams, lotions, shampoos, cream rinses, and ointments. It is now recognized that these kinds of topical formulations are unsuitable for administration shortly before the actual delivery of radiotherapy to the patient. Indeed, these product forms leave residues that can result in topical burning, including severe burns, when radiation is administered. Accordingly, there is a need in the art to provide a topical formulation that can be administered to a patient shortly before the actual delivery of radiotherapy.

SUMMARY OF THE INVENTION

Embodiments of the invention relate to pharmaceutical compositions for use in ameliorating an effect of radiotherapy on skin, mucous membranes, or hair follicles including a solvent and an effective prophylactic or therapeutic amount of a nitroxide radioprotector in solution in the solvent, preferably a solvent that is thickened or is in the form of a low-residue gel. Certain preferred embodiments the nitroxide radioprotector are TEMPO, 2,2,6,6-tetramethylpiperidine-1-oxyl, and TEMPOL, 4-hydroxy-2,2,6,6-tetramethylpiperidine-1-oxyl.

Pharmaceutical compositions can include solvents selected from the group consisting of water, urea, alcohols, and glycols. In embodiments where the solvent is an alcohol, the alcohol may advantageously be selected from the group consisting of methanol, ethanol, propanol, butanol, and the like. In embodiments where the solvent is a glycol, the glycol may advantageously be selected from the group consisting of ethylene glycol, propylene glycol, and the like. In certain embodiments, it is preferred to use water, or other non-irritating liquids, as a solvent for formulations to be administered to the mucous membranes. In additional embodiments, solvents used for mucous membrane formulations are not irritating (e.g., alcohol, urea, and the like).

In particular embodiments, pharmaceutical compounds described herein can ameliorate conditions caused or enhanced by radiotherapy including skin conditions, mucous membrane conditions, hair follicle conditions, and the like. In specific embodiments the particular skin conditions that the pharmaceutical compositions can treat or prevent include erythema, folliculitis, fibrosis, dry desquamation, moist desquamation, hyperpigmentation, dermatitis, and the like. In some embodiments, pharmaceutical compositions described herein can prevent mucous membrane conditions such as oral mucositis, proctitis, and the like, and are particularly valuable in protecting the rectal mucosa during radiotherapy of tumors in that area, such as prostate tumors. Additionally, in other embodiments the pharmaceutical compositions can treat or prevent hair follicle conditions such as alopecia, and the like.

In further embodiments, the effective prophylactic or therapeutic amount of the nitroxide radioprotector is an amount from about 0.01 to about 100 mg/ml of the formulation. Specific examples of particular amounts contemplated include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more mg/ml. In certain embodiments, the nitroxide radioprotector is 4-hydroxy-2,2,6,6-tetramethylpiperidine-1-oxyl.

Additional embodiments include pharmaceutical compositions including a polymer selected from the group consisting from ethylene polymers, acrylic polymers, polyvinylpyrrolidones (PVPs), polyvinyl copolymers, cellulose polymers, natural polymers, polystyrene polymers, silicone polymers, and inorganic polymers.

Further embodiments include pharmaceutical compositions having a viscosity such that the nitroxide radioprotector will remain in contact with a treated area for a sufficient period of time to allow absorption of a pharmacologically effective amount into said treated area.

Embodiments of the invention also include pharmaceutical compositions for use in ameliorating an effect of radiotherapy to skin, mucous membranes, or hair follicles including a solvent and an effective prophylactic or therapeutic amount of a nitroxide radioprotector in solution in the solvent, preferably wherein the pharmaceutical composition is thickened with a viscosity-enhancing agent, such as carboxymethylcellulose, a gum such as guar gum, an alginate, or other low-residue thickening agent, or is in the form of a low-residue gel. The thickening or gelling agent should be selected so as not to leave a sufficient residue to enhance burning to the skin or mucous membranes when radiotherapy is applied. In certain embodiments, the nitroxide radioprotector is 4-hydroxy-2,2,6,6-tetramethylpiperidine-1-oxyl.

Additional embodiments include pharmaceutical compositions for use in preventing or treating alopecia including a solvent and an effective prophylactic or therapeutic amount of 4-hydroxy-2,2,6,6-tetramethylpiperidine-1-oxyl in solution in the solvent, wherein the pharmaceutical composition is in the form of a low-residue gel.

Other embodiments include methods of treating a patient comprising topically applying a sufficient amount of nitroxide radioprotector to prevent or treat harmful side effects caused by radiotherapy, wherein the nitroxide radioprotector is in solution in a solvent. In preferred embodiments the nitroxide radioprotector is 4-hydroxy-2,2,6,6-tetramethylpiperidine-1-oxyl. Other advantageous embodiments include solutions in the form of a low-residue gel or thickened liquid. In certain embodiments, the solvent can be selected from the group consisting of water, urea, alcohols, and glycols. It is preferred that harmful side effects are selected from the group consisting of skin conditions such as erythema, folliculitis, fibrosis, dry desquamation, moist desquamation, hyperpigmentation, and dermatitis, mucous membrane conditions such as oral mucositis and proctitis, hair follicle conditions such as alopecia, cytotoxicity and polynucleic acid damage.

Additional embodiments include methods of treating a patient including topically applying a sufficient amount of nitroxide radioprotector to prevent or treat a harmful side effect caused by radiotherapy, wherein the nitroxide radioprotector is in solution in solvent, evaporating solvent, and applying radiotherapy to the patient. In certain embodiments, the nitroxide radioprotector is 4-hydroxy-2,2,6,6-tetramethylpiperidine-1-oxyl.

Further embodiments include methods of treating a patient, including topically applying a sufficient amount of nitroxide radioprotector to prevent or treat harmful side effects caused by radiotherapy, wherein the nitroxide radioprotector is in solution and is in the form of a low-residue gel or thickened liquid. In certain embodiments the nitroxide radioprotector is 4-hydroxy-2,2,6,6-tetramethylpiperidine-1-oxyl.

DETAILED DESCRIPTION

Radiotherapy and Cancer

Figure 1:
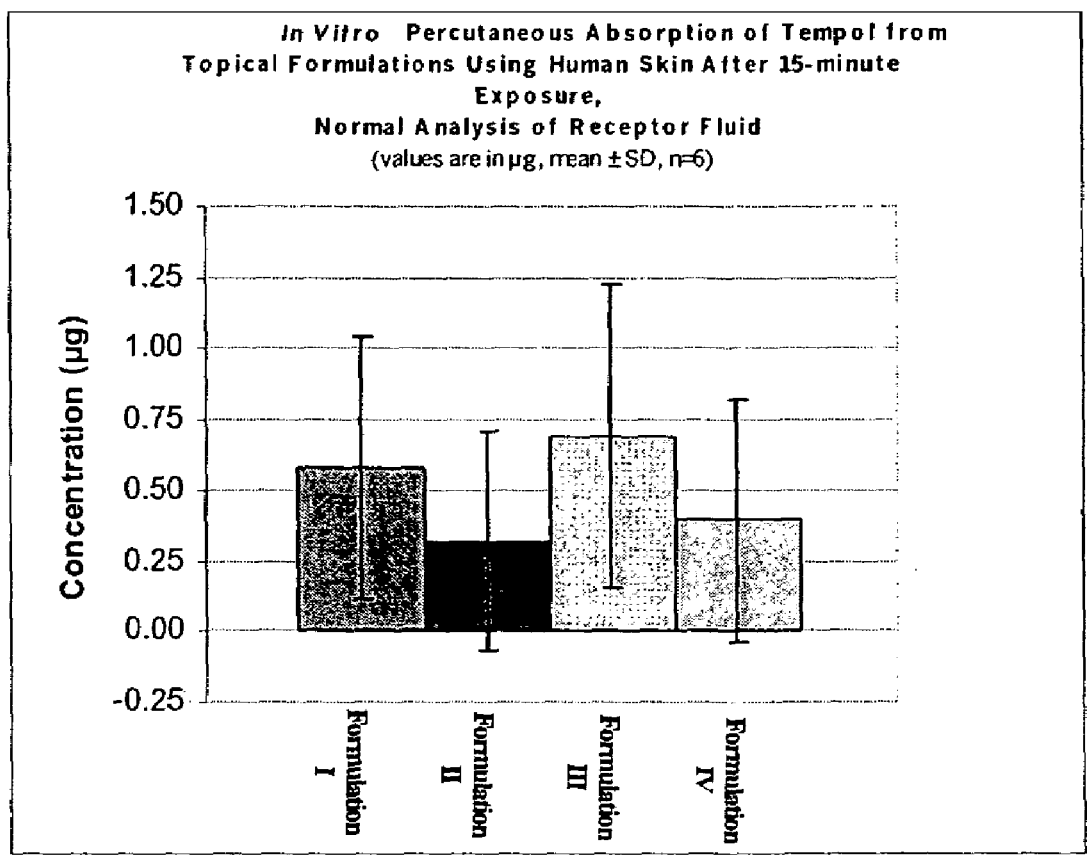
FIG. 1 is a bar graph providing the measured concentration of normal Tempol in receptor fluid after in vitro percutaneous absorption of four different topical Tempol formulations (Formulations I-IV) into human skin for 15 minutes.
Figure 2:
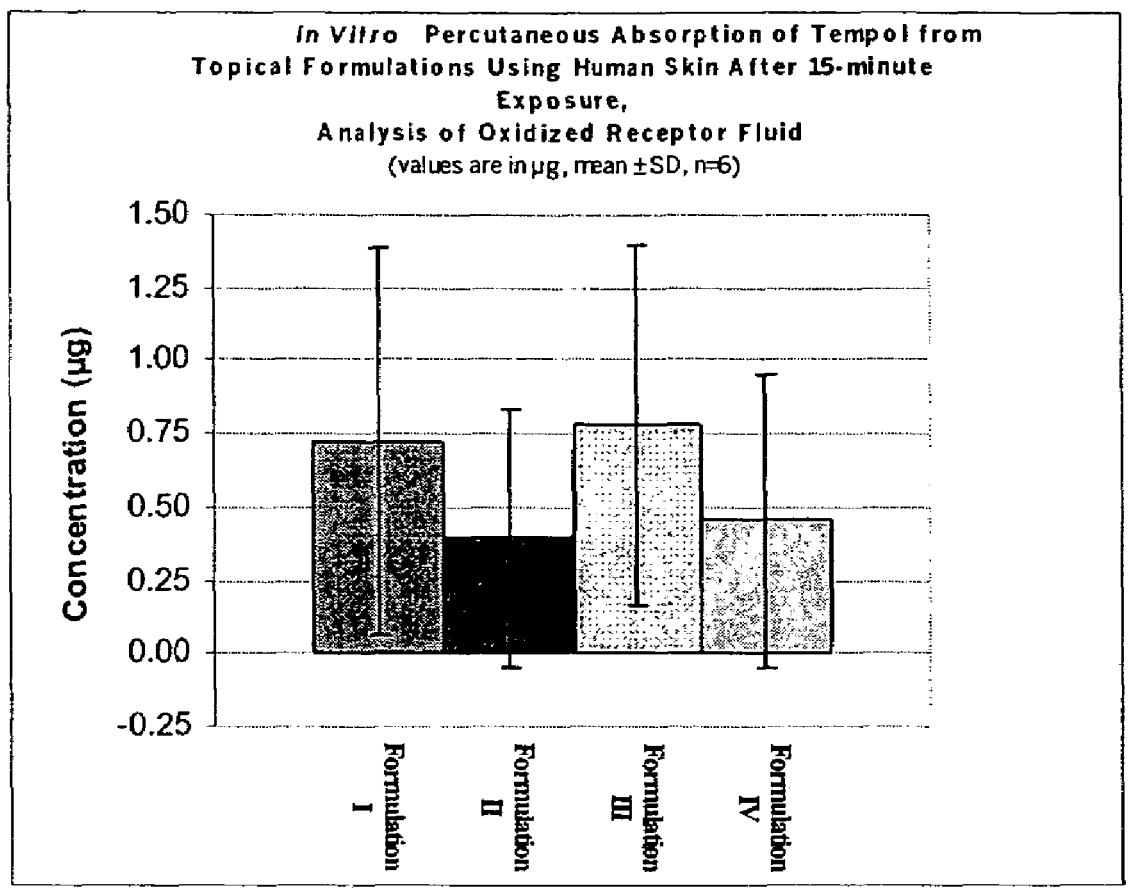
FIG. 2 is a bar graph providing the measured concentration of oxidized Tempol oxidized receptor fluid after in vitro percutaneous absorption of four different topical Tempol formulations (Formulations I-IV) into human skin for 15 minutes.
Figure 3:
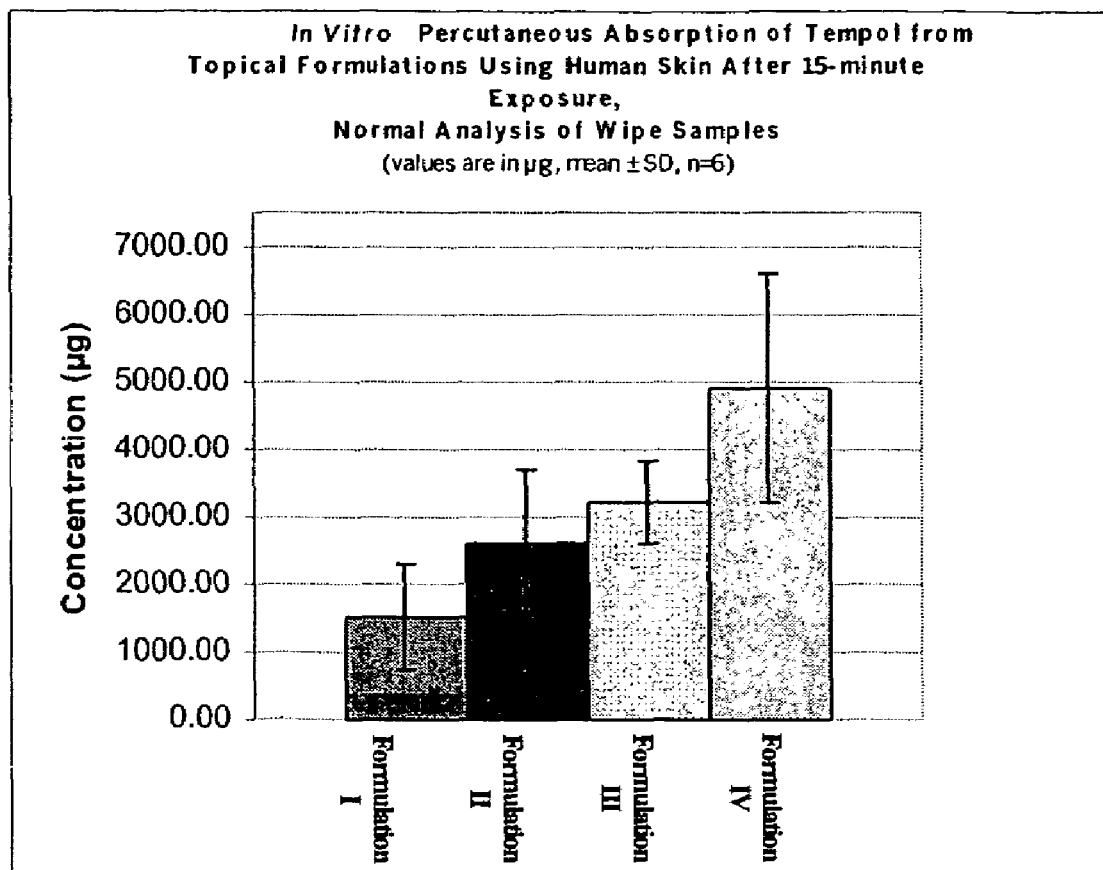
FIG. 3 is a bar graph providing the measured concentration of normal Tempol in wipe samples after in vitro percutaneous absorption of four different topical Tempol formulations (Formulations I-IV) into human skin for 15 minutes.
Figure 4:
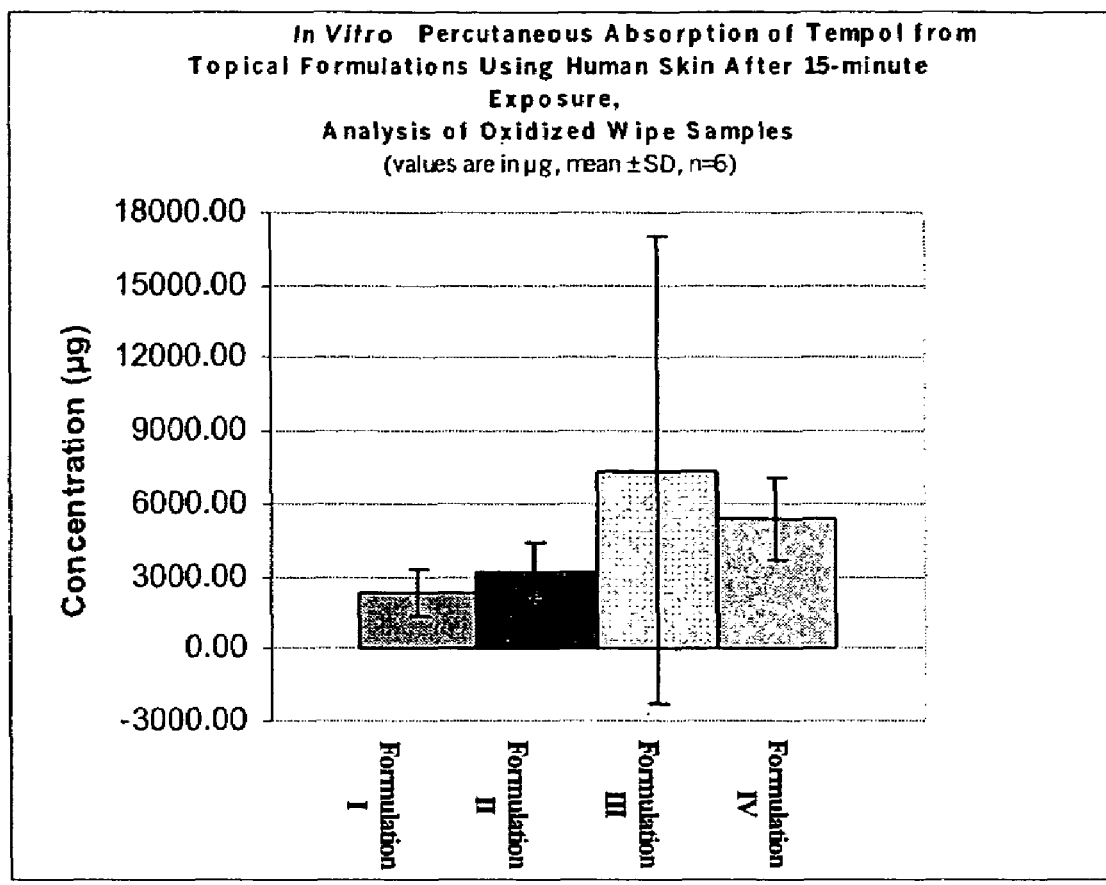
FIG. 4 is a bar graph providing the measured concentration of oxidized Tempol in wipe samples after in vitro percutaneous absorption of four different topical Tempol formulations (Formulations I-IV) into human skin for 15 minutes.
Figure 5:
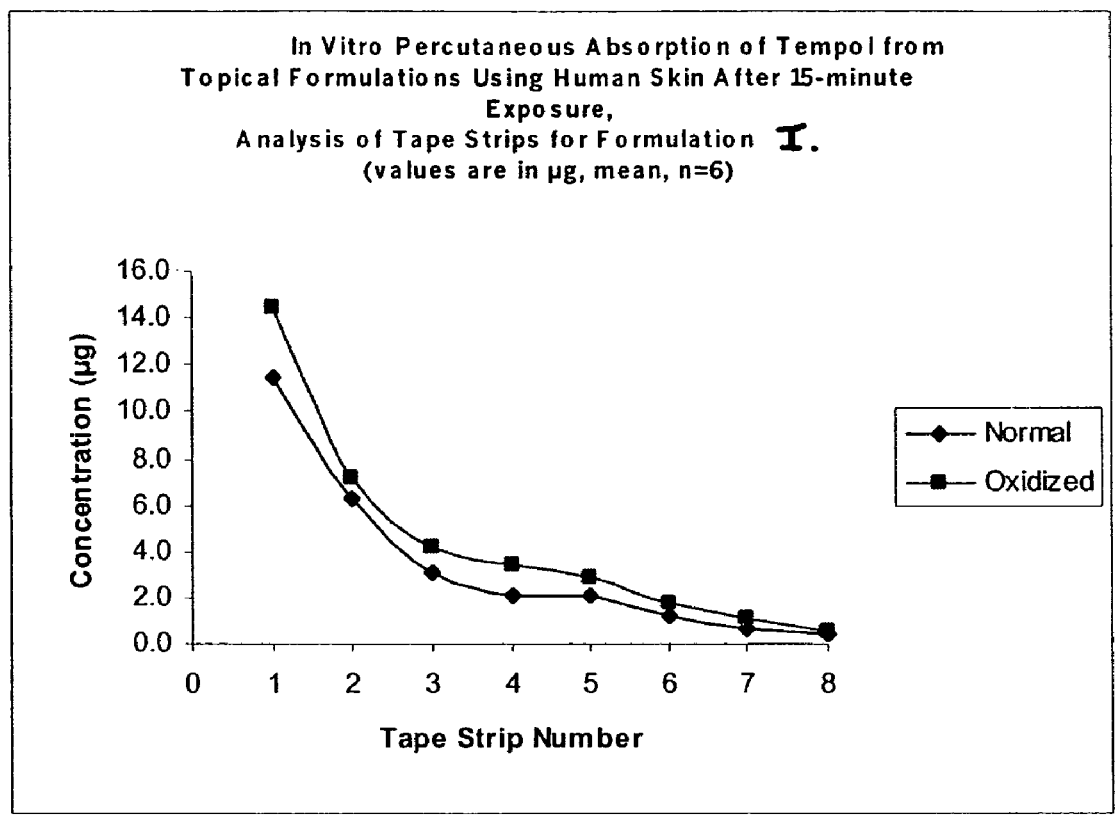
FIG. 5 is a line graph comparing the measured concentration of normal and oxidized Tempol in tape strips after in vitro percutaneous absorption of Formulation I into human skin for 15 minutes.
Figure 6:
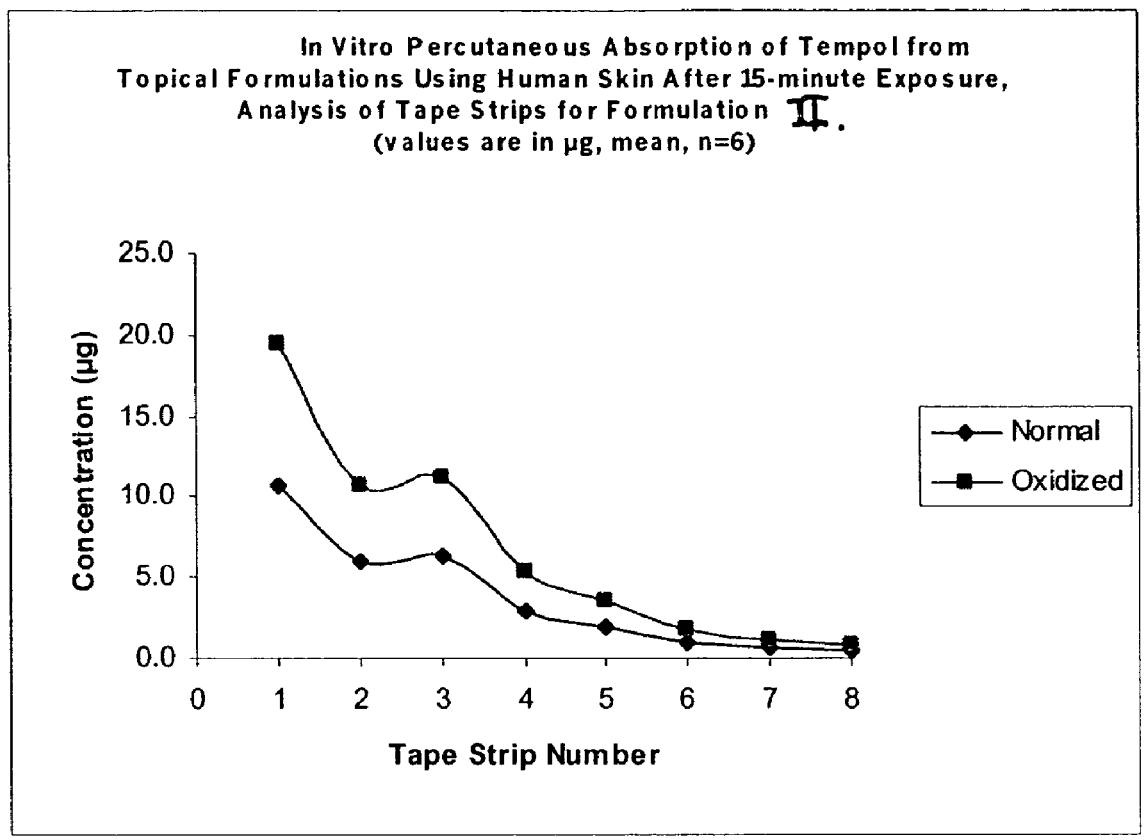
FIG. 6 is a line graph comparing the measured concentration of normal and oxidized Tempol in tape strips after in vitro percutaneous absorption of Formulation II into human skin for 15 minutes.
Figure 7:
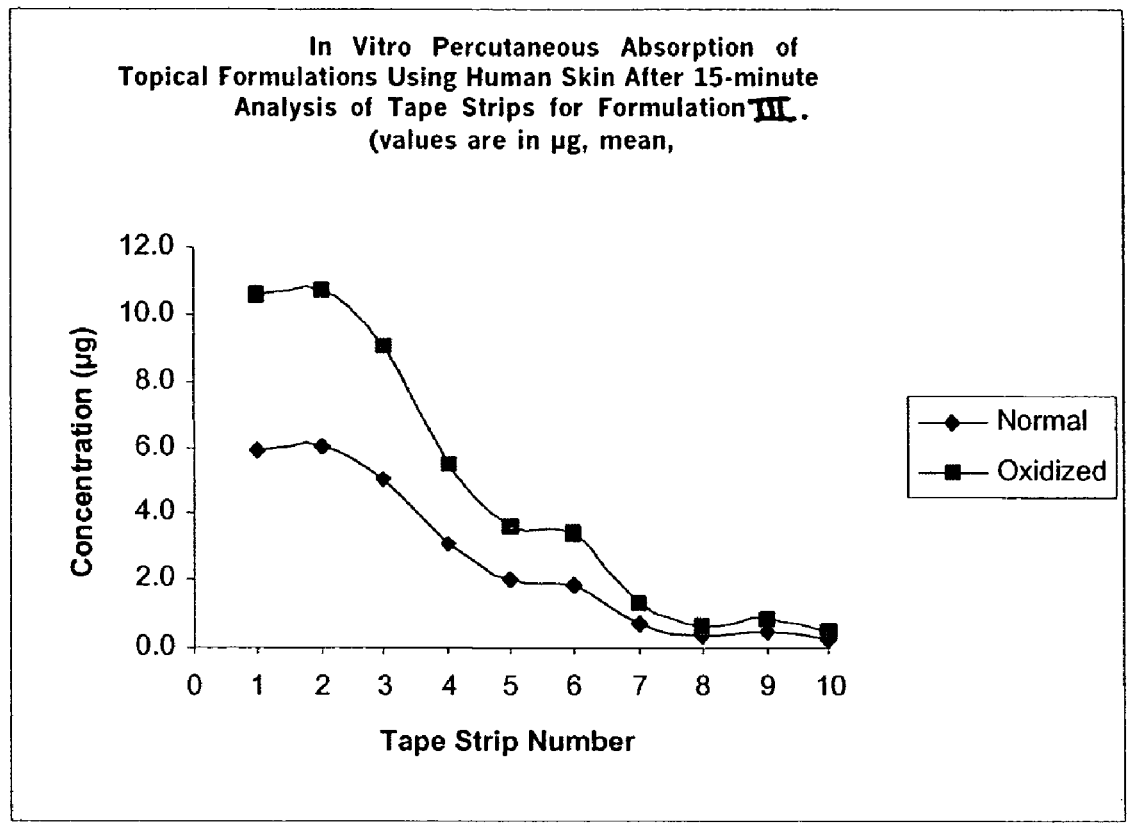
FIG. 7 is a line graph comparing the measured concentration of normal and oxidized Tempol in tape strips after in vitro percutaneous absorption of Formulation III into human skin for 15 minutes.
Figure 8:
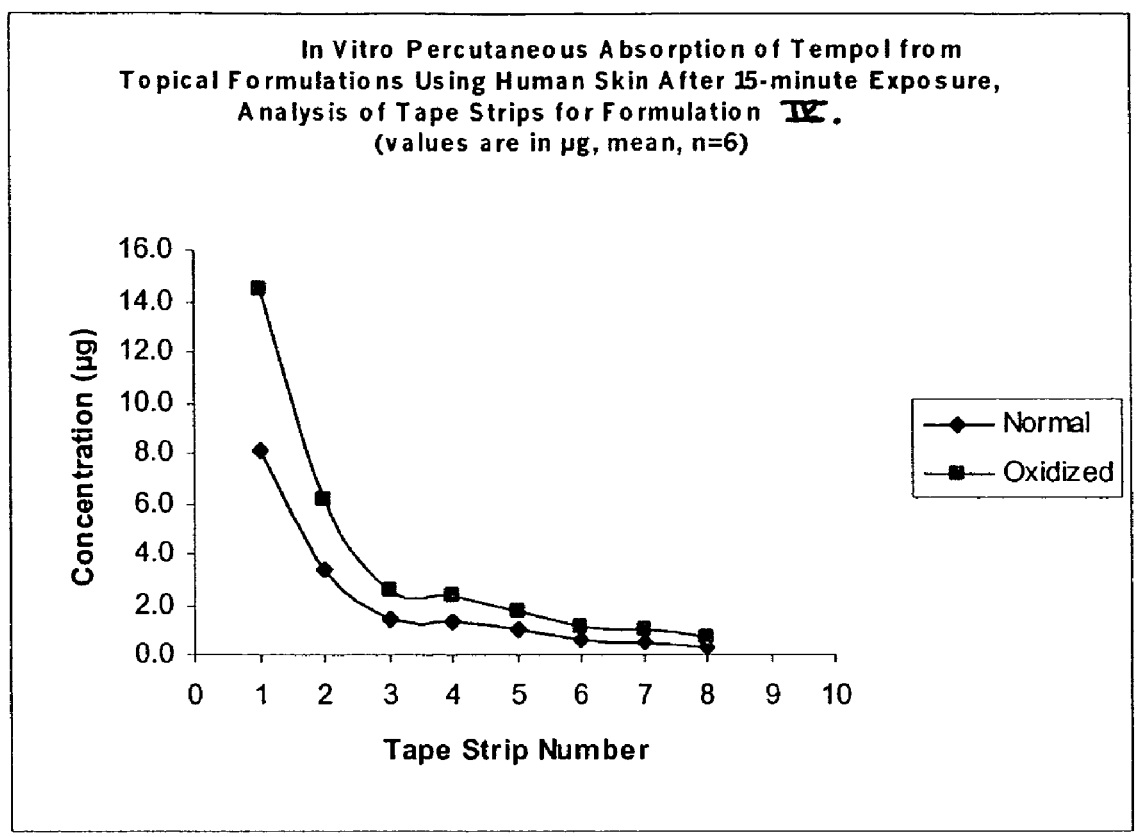
FIG. 8 is a line graph comparing the measured concentration of normal and oxidized Tempol in tape strips after in vitro percutaneous absorption of Formulation IV into human skin for 15 minutes.
Figure 9:
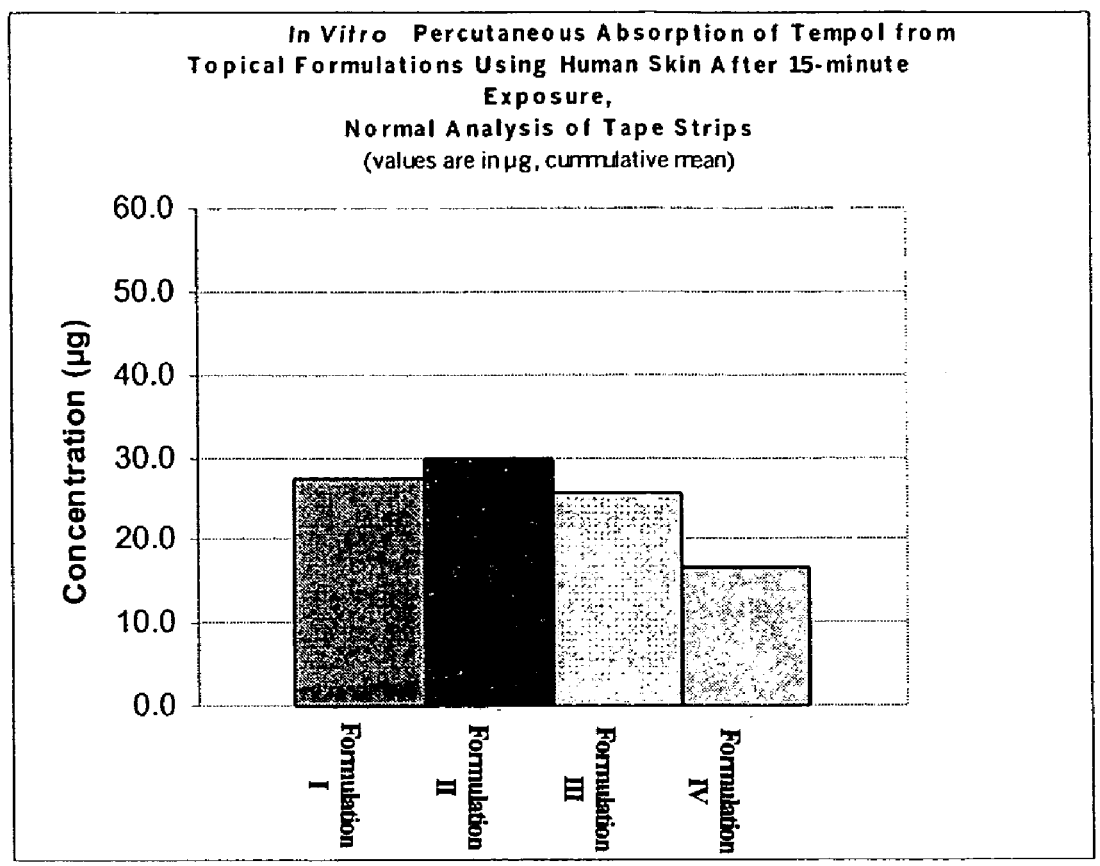
FIG. 9 is a bar graph providing the measured concentration of normal Tempol in tape strips after in vitro percutaneous absorption of four different topical Tempol formulations (Formulations I-IV) into human skin for 15 minutes.
Figure 10:
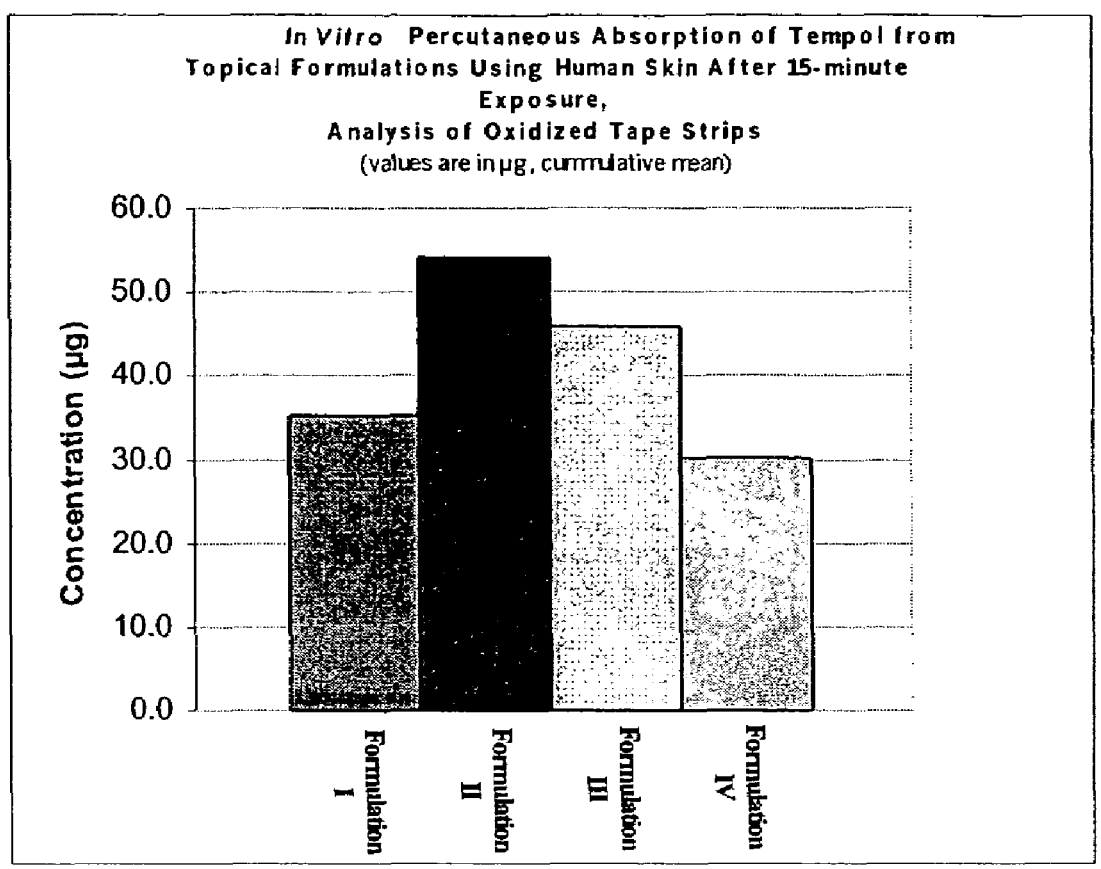
FIG. 10 is a bar graph providing the measured concentration of oxidized Tempol in tape strips after in vitro percutaneous absorption of four different topical Tempol formulations (Formulations I-IV) into human skin for 15 minutes.
Figure 11:
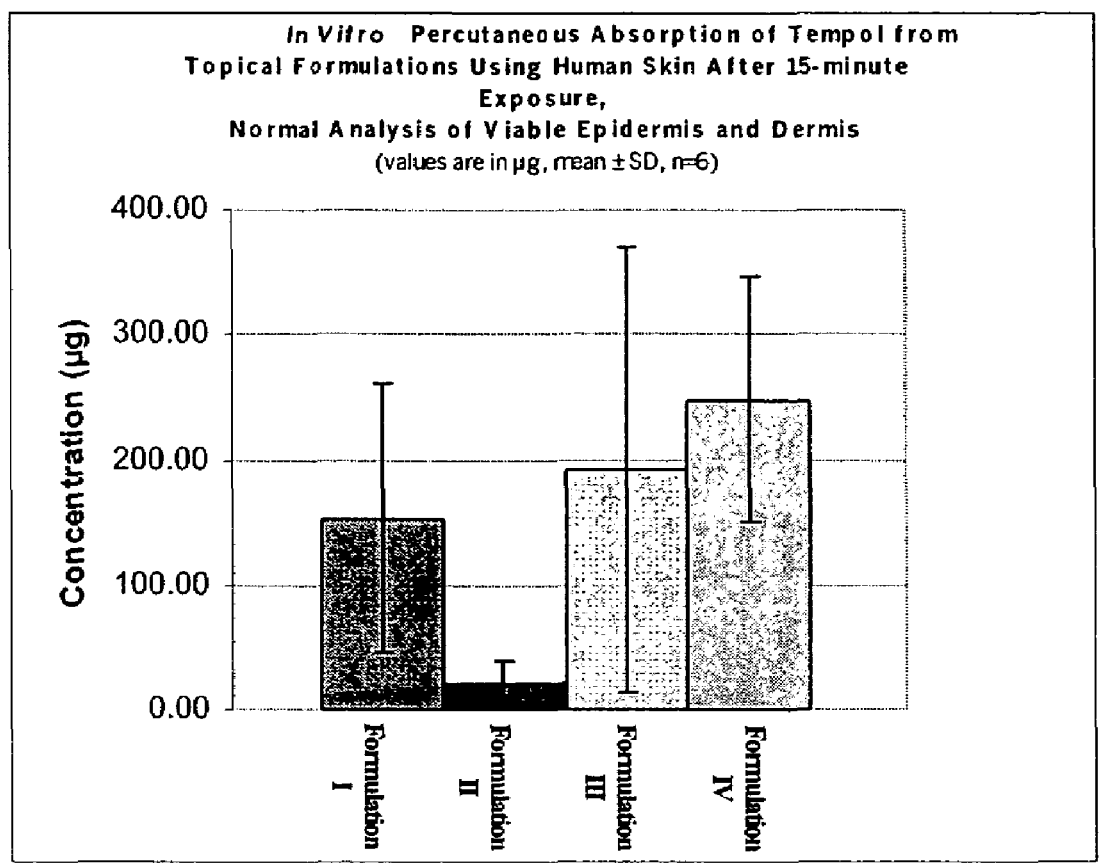
FIG. 11 is a bar graph providing the measured concentration of normal Tempol on viable epidermis and dermis after in vitro percutaneous absorption of four different topical Tempol formulations (Formulations I-IV) into human skin for 15 minutes.
Figure 12:
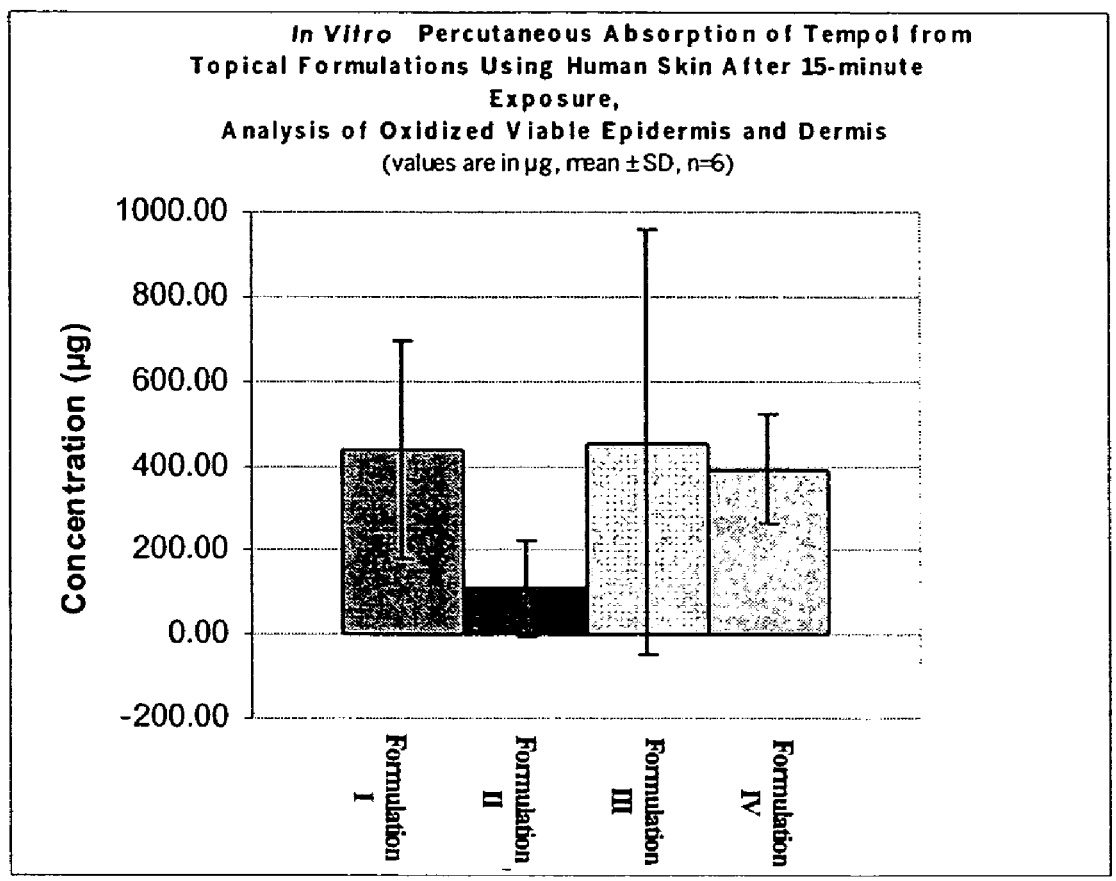
FIG. 12 is a bar graph providing the measured concentration of oxidized Tempol on viable epidermis and dermis after in vitro percutaneous absorption of four different topical Tempol formulations (Formulations I-IV) into human skin for 15 minutes.

Radiation therapy works by directing ionizing radiation into the area being treated with the goal of damaging the genetic material of cancerous cells thereby making it impossible for these cells to divide. Accordingly, radiotherapy is an important tool in the fight against cancer and is used in the treatment of as many as 50% of all cancer patients. In fact, more than half a million cancer patients receive radiation therapy each year, either alone or in conjunction with surgery, chemotherapy or other forms of cancer therapy. Other terms for radiotherapy include radiation therapy, x-ray therapy, electron beam therapy, cobalt therapy, or irradiation.

Radiotherapy is especially useful in cases where surgical removal of the cancer is not possible, where surgery might debilitate the patient, or where surgical debulking of the tumor has not absolutely removed all cancerous tissue. Radiotherapy is routinely used following surgery to destroy any cancer cells that were not removed by surgery. Further uses of radiotherapy are prior to surgery where it can "shrink" a previously inoperable tumor down to a manageable size to enable surgical excision.

Radiation therapy can also be used to help relieve symptoms of advanced cancer (such as bleeding or pain), even if a cure is not possible. Over one-third of the practice of radiation therapy is palliative. The typical intent of palliative treatment is to relieve pain quickly and maintain symptom control for the duration of the patient's life. Accordingly, treatment is usually tailored to the patient's clinical condition and overall prognosis. Palliative treatment is often complementary to analgesic drug therapies and may enhance their effectiveness because it can directly target the cause of pain.

Specifically, radiotherapy can be used to treat localized solid tumors, such as cancers of the skin, head and neck, brain, breast, prostate, cervix, and the like. Radiation therapy can also be used to treat cancers of the blood-forming cells and lymphatic system including leukemia and lymphoma respectively, and the like. Mucous membranes or hair in the vicinity of the radiation or in the path of the radiation (e.g., scalp hair in the case of a brain tumor and rectal mucosa in the case of prostate cancer) can be protected using the present invention.

Radiation Forms and Dosage

External beam radiation therapy commonly uses photons, which are sometimes called "packets of energy," to treat cancer. It is an object herein to ameliorate the negative effects of all radiotherapy regardless of the form of the photon or particle, including x-rays, gamma rays, UV rays including UV-A, UV-B and UV-C, neutrons, protons, and electrons including beta particles and the like.

X-rays are a very common form of radiation used in radiotherapy. Gamma rays are another form of photons used in radiotherapy. Gamma rays can be produced spontaneously as certain elements (such as radium, uranium, and cobalt 60), which release radiation as they decompose, or decay. Each element decays at a specific rate and can give off energy in the form of gamma rays and other particles. Typically x-rays and gamma rays have the same general effect on cancer cells.

External beam radiation therapy can be delivered by means of a linear accelerator. Typically, linear accelerators use powerful generators to create the high energy rays for external beam radiation therapy. Generally, linear accelerators are capable of producing x-rays at various energies. The linear accelerator can include a special set of lead shutters, called collimators, which focus and direct the rays to the tumor. The linear accelerator can be a large "L-shaped" design which allows it to rotate and deliver radiation from all angles. Multiple angles allow the maximum amount of radiation to be delivered to the tumor while delivering a minimal amount of radiation to the surrounding healthy tissue. The formulations and methods described herein can be used in conjunction with collimators or other devices and methods that limit radiation exposure to normal cells.

Formulations and methods described herein are capable of ameliorating the effects of most forms of radiotherapy. For example, the compositions and methods can ameliorate the effects of local-field radiation and wide-field radiation. Local field radiation relates to a narrow beam of radiation directed at the specific metastatic site or sites. Customarily, local field radiation has tended to be used for patients with a long life expectancy and fewer metastatic sites. In contrast, wide-field radiation employs a larger field of radiation and is often used to treat patients with a shorter life expectancy and multiple metastatic pain-causing sites.

Radiotherapy dosage is measured by the scientific unit rad (radiation absorbed dose) which is a radiation energy dose equal to an energy of 100 ergs per gram of irradiated material. A patient who receives radiation therapy as a treatment for cancer can receive several thousand rads over a very short period of time (weeks or months). In contrast, a typical scanning x-ray contains far fewer rads. For example, modern mammography systems used to take x-ray images of the breast use approximately 0.1 to 0.2 rad dose per x-ray.

According to traditional radiotherapy, the larger the daily dose of radiation, the lower the total dose that can be administered because of limits to normal tissue tolerance. Proportionately more tumor cells are killed when the daily radiation dose is larger. Typically a balance is obtained between the killing of tumor cells and the adverse radiation effects on normal tissues, which are largely a function of the daily dose. A number of different schedules have been developed that take into account specific tumor characteristics and the tolerance of normal tissues. The literature is divided regarding the optimal radiation schedule to achieve tumor regression and disease palliation of either primary or metastatic sites. Generally, however, radiation treatment is planned in relation to clinical status. Because a main objective herein is to ameliorate the negative effects of radiation therapy, normal tissue can have a higher tolerance to radiation therapy and larger dosages of radiation can be administered safely.

Side Effects of Radiation

In general, radiation therapy is a local treatment. It typically affects the cells in the treated area. However, as mentioned above, in addition to damaging cancer cells, radiation can also damage normal cells located in the treated area. Normal cells that are located in the treated area can include skin cells, mucous membranes, hair follicles, and the like.

Radiation side effects are typically restricted to the radiation portal and can be classified as either acute, occurring during or immediately after the course of radiation therapy, or late, occurring months to years later. Acute radiation effects are more prominent with radiation schedules that deliver high total doses of radiation with small daily fractions; they generally begin at the end of the second week of therapy. Acute radiation effects, occurring primarily at skin and mucosal surfaces, usually consist of an inflammatory response such as skin erythema or pigmentation, or as mucositis. Late radiation effects may arise without any preceding acute reactions.

Fibrosis is the most common type of late radiation injury and can be observed in many types of tissue, including skin.

Other skin conditions caused by radiation therapy include dry and moist desquamation. Dry desquamation, which is characterized by dry and flaky skin and pruritus in the area of irradiation. Moist desquamation, is characterized by sloughing of the epidermis, exposing the moist, raw, dermis layer of the skin.

The rate at which particular hair cells grow is directly proportional to their sensitivity to radiotherapy. Accordingly, the following lists represents particular hair cells' sensitivity to radiotherapy in decreasing order: scalp hair, male beard, eyebrows axilla, pubis, and lastly fine hair. The hair follicle's epithelium is derived from the epidermis and is similarly radiosensitive. As a result, the follicular cells may develop an acute dermatitis, or hyperpigmentation earlier than other cells in the dermis. Hair follicles' sensitivity to radiation can often lead to alopecia in a patient undergoing radiotherapy.

One objective described herein is to ameliorate the negative effects of radiation therapy on normal cells, regardless of whether the effect is acute or late, or whether the effect relates to the patient's skin, mucous membranes, hair follicles, or other treated areas.

Nitroxide Radioprotectors

The term nitroxide radioprotectors, as used herein, includes any nitroxide capable of ameliorating an effect of radiotherapy. Typically nitroxides relate to stable free radical compounds that can react with a variety of biologically relevant compounds, including other free radicals, such as OH and H. Generally nitroxide radioprotectors can ameliorate most of the effects of radiotherapy including, but not limited to, protecting against cytotoxicity and polynucleic acid (e.g., DNA, RNA) damage, including mutagenicity. Further examples of effects that nitroxide radioprotectors can ameliorate include, but are not limited to skin conditions, mucous membrane conditions, and hair follicle conditions. In certain embodiments nitroxide radioprotectors include nitroxides that can react with oxy radicals, such as antioxidants, for example. In additional embodiments, nitroxide radioprotectors can neutralize superoxides and hydrogen peroxide.

According to certain embodiments the nitroxide radioprotector can be selected from the following formulas:

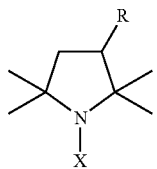

Wherein X is selected from O. and OH, and R is selected from COOH, CONH, CN, and CH$_2$NH$_2$

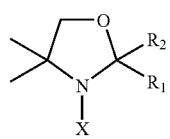

Wherein X is selected from O. and OH, and R$_1$ is selected from CH$_3$ and and R$_2$ is selected from C$_2$H$_5$ and spirocyclohexyl

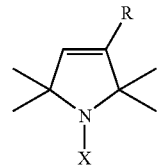

Wherein X is selected from O. and OH and R is selected from CONH.

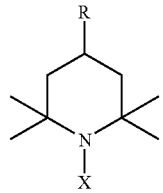

Wherein X is selected from O. and OH and R is selected from H, OH, and NH$_2$ and T is selected from O.

Suitable Nitroxide radioprotectors can also be found in Proctor, U.S. Pat. No. 5,352,442, and Mitchell et al., U.S. Pat. No. 5,462,946, both of which are hereby incorporated by reference in their entireties.

A non-limiting list of nitroxide radioprotectors include, 2-ethyl-2,5,5-trimethyl-3-oxazolidine-1-oxyl (OXANO), 2,2,6,6-tetramethylpiperidine-1-oxyl (TEMPO), 4-hydroxy-2,2,6,6-tetramethylpiperidine-1-oxyl (TEMPOL), 4-amino-2,2,6,6-tetramethyl-1-piperidinyloxy (Tempamine), 3-Aminomethyl-PROXYL, 3-Cyano-PROXYL, 3-Carbamoyl-PROXYL, 3-Carboxy-PROXYL, and 4-Oxo-TEMPO. These materials can be used as the sole active ingredient, or can be used with hair-growth-promoters such as Nicorandil and Minoxidil.

As used herein, nitroxide radioprotectors are solutes dissolved in a suitable solvent. This is to be distinguished from dispersions, suspensions, or emulsions of nitroxide radioprotectors, as were used in the prior art.

Although at least one nitroxide radioprotector is an active ingredient in all compositions described herein, these compositions can also include other active ingredients that are capable of ameliorating the negative effects of radiotherapy or chemotherapy. Accordingly, nitroxide radioprotectors can be used alone or in combination with other nitroxide radioprotectors, hair growth stimulants or additaments. Other hair growth stimulants and additaments include hydroxyl radical scavengers, antiandrogens and other compounds described in International Publication No. WO 87/00427 and European Patent application No. 89300785.6, both of which are hereby incorporated by reference in their entirety. In certain embodiments, nitroxide radioprotectors can be used along with other anti-oxidative agents such as glutathione and the like.

Nitroxide radioprotectors can ameliorate numerous negative effects of radiotherapy including conditions to the skin, mucous membranes, hair follicles, and the like. Skin conditions that nitroxide radioprotectors can help prevent or treat include erythema, folliculitis, fibrosis, dry desquamation moist desquamation, hyperpigmentation and dermatitis and the like. Mucous membrane conditions that nitroxide radioprotectors can help prevent or treat include oral mucositis, proctitis, and the like. Nitroxide radioprotectors can also help prevent or treat alopecia and the like by stimulating hair growth. Stimulating hair growth can include increasing rate of growth, increasing hair diameter, follicular neogenesis, and the like. Nitroxide radioprotectors can also inhibit hair loss or alopecia from progressing.

Further embodiments herein include methods of preventing or treating hair loss or alopecia regardless of whether the condition was brought about by radiation therapy or other means. For example, it is well known that hair loss or alopecia can result from genetic factors, aging, local skin conditions, systemic diseases, and chemotherapy, for example. Those with skill in the art will recognize that the embodiments described herein encompass compositions and methods relating to formulations that are effective at treating or preventing any type of hair loss without leaving an unwanted residue on the treated area. Further embodiments include compositions and methods relating to formulations that are effective at treating or preventing any type of hair loss and have a sufficient viscosity such that the formulation does not immediately run off the treated area upon application to a patient.

Developing low-residue formulations can be done by preparing solutions of nitroxide radioprotectors in low-residue gels, thickened liquids, liquids and the like. Developing low-residue formulations with sufficient viscosity can be done by preparing solutions of nitroxide radioprotectors in low-residue gels or thickened liquids.

In certain embodiments, the nitroxide radioprotector is present in a topical solution at between approximately 5-15% by weight. In other embodiments, the nitroxide radioprotector is present in a topical solution at between approximately 7-12% by weight. In more specific embodiments, the nitroxide radioprotector makes up 7% by weight of the topical solution. Preferably the nitroxide radioprotector is dissolved in an ethanol based solution.

A gel according to the present invention will typically comprise a major amount of a liquid phase and a minor amount of a thickening or gelling agent. The gelling agent, in preferred embodiments, will comprise only 5%, 4%, 3%, 2%, 1%, 0.5% or less of the total volume or weight of the composition; thus, when applied to the skin or mucosa, the liquid can evaporate, leaving only the gelling agent and the active ingredient. In this manner, 98%, 99%, or more of the carrier for the drug can disappear prior to radiotherapy, greatly reducing or eliminating topical burning due to the bolus effect.

It should be noted that in a preferred embodiment of the invention, the liquid phase of a rectal gel (or other gel for mucosal use) is specifically selected for non-irritating mucosal properties. Thus, an aqueous vehicle is appropriate, as well as non-irritating alcohols (such as glycols or polyols) and other non-irritating solvents. It may be desirable, in practicing the present invention, to rectally administer an effective, radioprotective quantity of a nitroxide gel, and then preferably to retain the gel in the rectum during radiotherapy, or less preferably to remove the gel prior to radiotherapy.

Tempol

As mentioned above, one preferred nitroxide radioprotector that can be used in the pharmaceutical formulations described herein is Tempol. Tempol is a stable nitroxide radical which is readily available from commercial suppliers. Tempol is characterized by the chemical formula 4-hydroxy-2,2,6,6-tetramethylpiperidine-1-oxyl.

Tempol can ameliorate numerous negative effects of radiotherapy including conditions to the skin, mucous membranes, hair follicles, and the like. Skin conditions that Tempol can help prevent or treat include erythema, folliculitis, fibrosis, dry desquamation moist desquamation, hyperpigmentation, dermatitis, and the like. Mucous membrane conditions that Tempol can help prevent or treat include oral mucositis, proctitis, and the like. Hair follicle conditions that Tempol can help prevent or treat include alopecia and the like by stimulating hair growth. Stimulating hair growth relates to increasing rate of growth, increasing hair diameter, follicular neogenesis and the like. Tempol is also capable of inhibiting hair loss or alopecia from progressing.

As mentioned in the Background, the prior art has limited the topical use of Tempol to the formulations selected from creams, lotions, shampoos, cream rinses, and ointments. This invention focuses on the discovery that prior art topical forms of Tempol should not be administered shortly before the actual delivery of radiotherapy to the patient. These prior art topical formulations leave a residue or film on the patient's treated area (e.g., skin, mucous membranes). If this residue or film is left on the treated area before radiotherapy, it can intensify or absorb the radiation and can cause potentially severe burning. This burning caused by the residue or film can be described as a bolus effect. (See generally, Hilderley, *Oncology Nursing Forum*, vol. 10 No. 1, pp. 51-56 (1983)) Accordingly, compositions and methods herein include topical formulations that can be administered to a patient shortly before the actual delivery of radiotherapy. This can be done by topically applying Tempol in the form of a low-residue formulation, including, but not limited to solutions of Tempol in low-residue gels, thickened liquids, liquids and the like.

Suitable Solvents

Nitroxide radioprotectors, such as Tempol, are readably soluble in aqueous solutions. In some embodiments nitroxide radioprotectors can be dissolved in a solvent and prepared into a formulation including low-residue gels, low-residue thickened liquids, and low-residue liquids. Those skilled in the art will readily appreciate that any water miscible liquid, at appropriate levels, can be used as a solvent, including, but not limited to, glycerin, PEG's, polysorbates, etc. Because a main objective of the formulations and methods provided herein is to prepare low-residue nitroxide radioprotector formulations, embodiments herein include solvents that are relatively volatile. The term "relatively volatile" relates to solvents that are readily vaporizable at relatively low temperatures. For example, embodiments herein include solvents that are readily vaporizable between about 0-38° C. Such liquids, for example, may advantageously have a vapor pressure of at least 50 mmHg at 25° C., and more preferably a vapor pressure of at least 75, 90, 100, 150, 200, 250, or 300 mmHg. Accordingly, further embodiments include formulations and methods wherein the solvent has completely or substantially evaporated prior to the application of radiotherapy to the treated area.

The following is a non-exclusive list of solvents that can be used as a solvent for nitroxide radioprotectors: water, urea, alcohols and glycols. Any alcohol capable of dissolving nitroxide radioprotectors can be used in the formulations and methods described herein; examples include methanol, ethanol, propanol, butanol and the like. Likewise, any glycol capable of dissolving nitroxide radioprotectors can be used in the formulations and methods described herein; examples include ethylene glycol, propylene glycol and the like. In one preferred embodiment, the solvent not only dissolves the nitroxide radioprotector, but also facilitates transdermal delivery. Thus, transdermal-delivery-facilitating agents, particular those that disrupt or solubilize components of the stratum corneum, are particularly preferred. We have found that various alcohols, for example, facilitate penetration of nitroxide radioprotectors into the skin. Additional embodiments include available transdermal enhancers that allow for systemic treatment of a patient.

In certain embodiments of the invention, the concentration of the active ingredient, a nitroxide radioprotector, can be at a concentration level at or near its solubility limit. For example a nitroxide radioprotector can be about 80%, 81%, 82%, 83%, 84%, 85%, 86%, 87%, 88%, 89%, 90%, 91%, 92%, 93%, 94%, 95%, 96%, 97%, 98%, 99% and 100% of saturation in the solution. Embodiments also include formulations where a nitroxide radioprotector is soluble enough in the solvent to promote its release at the desired rate upon application to the treated area.

In certain embodiments, the solvent can comprise between approximately 70-90% of the solution. In other embodiments, the solvent comprises between approximately 75-86% of the solution. In more specific embodiments, the solvent comprises approximately 79% of the solution.

All of the above described solvents can be used with both the low-residue gels, thickened liquids and liquids described herein.

Characteristics of Nitroxide Radioprotector Formulations

Embodiments herein include topical formulations containing a nitroxide radioprotector dissolved in solution. All of the solvents described above can be used in the formulations described herein.

Topical formulations can be prepared such that they can readily be applied to all areas of a patients skin, including the scalp, face, neck, chest, arms, legs, torso, back, and the like. Topical formulations can also be prepared such that they can be applied to all mucous membranes of a patient including areas of the eyes, mouth, nose, vagina, rectum, and the like. In certain embodiments it is preferred that formulations used to treat mucous membranes include water, or another non-irritating solvents. In additional embodiments, the formulations to be applied to mucous membranes lack irritating solvents such as alcohol, urea, and the like.

In topical formulations, the total quantity of a nitroxide radioprotector or other active ingredients absorbed can vary greatly based on many factors including application area size, the frequency and vigor of application, and the viscosity or thickness of the applied vehicle. Other factors influencing drug absorption are the application site, age and condition of the skin. For example, non-keratinized, aged, broken or abraded skin will result in higher drug absorption, because these skin types are more readily penetrated by an active ingredient. Accordingly, one embodiment herein is to optimize the absorption of a nitroxide radioprotector by the treated patient while maintaining a low-residue formulation.

Because a primary objective herein is to ameliorate the negative effects of radiotherapy while not enhancing a bolus effect, topical composition embodiments should be low-residue. As used herein, the term "low-residue" refers to formulations that can be applied to a patient, shortly before undergoing radiotherapy, without leaving a residue capable of enhancing a bolus effect upon delivering radiotherapy to the treated area. Any low-residue formulation can be used according to the methods described herein. Low-residue formulations include, but are not limited to, gels, liquids, thickened liquids, and the like. Those with skill in the art can readily appreciate how to prepare low-residue gels, low-residue liquids, and low-residue thickened liquids to be used according to the methods described herein.

Other embodiments include topical formulations with sufficient viscosity such that the formulation does not immediately run off the treated area upon application. In certain embodiments the pharmaceutical composition should have a viscosity that keeps the nitroxide radioprotector and other active ingredients in contact with the treated area for a sufficient period of time to allow suitable absorption to the treated area. In some embodiments, gels and thickened liquid formulations can have a suitable viscosity such that the formulation will not immediately run off the treated area. Accordingly, methods of retaining the formulation in place are encompassed herein. As mentioned above, regardless of the composition's viscosity, there should not be a residue sufficient to produce a dangerous bolus effect when radiotherapy is applied to the treated area.

Alternative embodiments include topical formulations with low viscosity, including, but not limited to, low-residue liquids and low-residue thickened liquids. In some embodiments, liquids and thickened liquids can be applied with the aid of an applicator to allow suitable application of the nitroxide radioprotector to the treated area. Applicators can include, but are not limited to, cloths, rags, sponges, towels, gauze, and like absorbent materials, and the combination of the applicator and the nitroxide radioprotector solution is one aspect of the methods described herein.

In addition to including a nitroxide radioprotector and a solvent, the topical compositions herein can also include polymers, colorants, antimicrobials, preservatives, antioxidants, alcohols, emollients, additional active ingredients, ingredients that enhance the permeability of the treated area, water, and other ingredients commonly used in low-residue topical formulations. Additional ingredients in the compositions herein are acceptable as long as the formulation, as a whole, remains low residue.

Those with skill in the art can readily modify the thickness of nitroxide radioprotector formulations, whether gels or liquids, with polymers. Embodiments include formulations including one or more suitable polymers with moderate to high degree of compatibility with the solvent used to dissolve the nitroxide radioprotector. In certain embodiments the polymers can be selected from ethylene polymers, acrylic polymers, polyvinylpyrrolidones (PVPs), polyvinyl copolymers, cellulose polymers, including modified cellulose, natural polymers including collagen, polystyrene polymers, silicone polymers, inorganic polymers, and the like.

Examples of ethylene polymers that can be used include, but are not limited to, oxidized polyethylene, polyethylene, polyethylene glycol, and the like.

Examples of acrylic polymers that can be used include, but are not limited to, acrylic esters, methacrylic esters copolymer, acrylic polymer emulsion, carbomer, ethylene acrylates, methacryiol ethyl betaine, methacrylates copolymer, octylacrylamide, acrylates, butylaminoethyl methacrylate copolymer, polyacrylamidomethylpropane sulfonic acid, polyquaternium-5, polyquaternium-6, polyquaternium-7, polyquaternium-15, and the like.

Examples of polyvinylpyrrolidones (PVPs) include, but are not limited to, polyquaternium-11, polyvinylpyrrolidone (PVP), PVP/dimethylaminoethylmethacrylate copolymers, PVP/Elcosene copolymer, PVP/ethyl methacrylate/methacrylic acid terpolymer. PVP/hexadecene copolymer, PVP/VA copolymers, styrene/PVP copolymer, and the like.

Examples of polyvinyl copolymers include, but are not limited to, ethylene vinyl acetate copolymer, PVM/MA copolymer esters, vinyl acetate/crotonic acid copolymer, vinyl acetate/crotonic acid/methacryloxybenzophenone-1 copolymer, vinyl acetate/cotonic acid/vinyl neodecanoate copolymer, carboxymethyl cellulose, hydroxyethyl cellulose, hydroxypropyl cellulose, hydroxypropyl methylcellulose, PEG celluloses, polyquaternium-4, polyquaternium-10, and the like.

Examples of natural polymers include, but are not limited to, acacia, agar, alginate, carrageenan, furcelleran, gelatin, ghatti gum, glycosaminoglycans, guar gum, guar gum derivative, hydroxypropyl guar, hyaluronic acid, karaya, locust bean gum, maltodextrin, pectin, tragacanth gum, xanthan, and the like.

Examples of polystyrene polymers include, but are not limited to, sodium polystyrene sulfonate.

Examples of silicone polymers include amino bispropyl dimethicone, cyclomethicone, dimethicone, dimethicone copolyol, hexamethyldisiloxane, methicone, octadecyl dimethicone, phenyl dimethicone, stearoxy dimethicone, and the like.

Examples of inorganic polymers, include but are not limited to bentonite, modified bentonite, magnesium aluminum silicate, modified hectorite, sodium magnesium silicate, and the like.

The above listed polymers can be used in all compositions described herein, For example, the polymers can be used in low-residue gels. The polymers can also be used as thickening agents in low-residue thickened liquids.

Gels

As discussed above, in some embodiments, the pharmaceutical composition is a topical formulation in the form of a low-residue gel. As used herein, a gel relates to a semisolid system of either suspensions made up of small inorganic particles or large organic molecules interpenetrated by a liquid. Generally, if left undisturbed for some time, gels may be in a semisolid or gelatinous state. With some gels, small amounts of water may separate on standing.

Those with skill in the art will readily know how to prepare low-residue gels. Detail on how to prepare such gels is provided in Remington's Pharmaceutical Sciences, 18$^{th}$ ed. 1990, which is hereby incorporated by reference in its entirety. In one embodiment a gel can be prepared by slowly dispersing one or more suitable polymers in the requisite amount of suitable solvents. A discussion of suitable solvents and polymers is provided above. According to one method of preparation, a polymer and a solvent can be stirred until the polymer is completely dissolved. Water can be added to the polymer/solvent solution as it is being stirred. A sufficient amount of a nitroxide radioprotector can be added to the stirred mixture until the nitroxide radioprotector is adequately dissolved.

Gels can be one-phase or multiple phase systems. A gel mass consisting of a network of small discrete particles is generally termed a two-phase system while singe-phase gels typically consist of organic macromolecules distributed uniformly throughout a liquid in such a manner that no apparent boundaries exist between the dispersed macromolecules and the liquid.

In certain embodiments, the low-residue gel can be a hydroalcoholic gel. In some embodiments an alcohol such as ethanol can be used to dissolve the nitroxide radioprotector while avoiding the use of solubilizers such as PEG-40, hydrogenated castor oil, polysorbate 20 or similar ingredients. The absence of these solubilizers can greatly improve the cosmetic feel of the product as the stickiness and rubbery feel can be virtually absent. In embodiments where the pharmaceutical composition has a significant alcohol (e.g., ethanol) content, additional preservation may not be required.

Those with skill in the art can use numerous methods to readily prepare hydroalcohol gels with the formulation characteristics described herein. According to one method of preparing hydroalcohol gels, a solution can be prepared by dissolving the nitroxide radioprotector in ethanol. The nitroxide radioprotector/ethanol solution can be added to a hydrogel. According to certain embodiments, the nitroxide radioprotector/ethanol solution can be added to a premade hydrogel using a slow moving anchor mixer, which can reduce the creation of air bubbles in the hydroalcohol gel.

Due to reduced hydrogen bonding, the viscosity of a hydroalcoholic gel is generally lower than the viscosity of a corresponding hydrogel. Regardless those with skill in the art can adjust the ingredients of the hydroalcoholic gel to prepare a composition with a suitable viscosity tailored to the desired characteristics. For example the use of the thickening agents or polymers discussed above can be used to raise the viscosity of a particular formulation.

In some embodiments the low-residue gel can be sprayable. Methods of preparing sprayable gels are well known in the art. According to one embodiment of preparing a sprayable gel, a suitable polymer can be added to water. Upon hydration and development of structure, the thickened polymer/water mixture can be added to a nitroxide radioprotector/solvent solution.

Liquid Formulations

Further embodiments herein include nitroxide radioprotector-containing liquid formulations. For example, a nitroxide radioprotector can be dissolved in any of the suitable solvents discussed above. The following is a non-exclusive list of solvents that can be used as a solvent for Tempol: water, urea, alcohols, glycols and the like. These liquid formulations can be used with the aid of an applicator such as a towel, cloth, rag, sponge, gauze or like absorbent material in order to apply the formulation to a patient in need.

Further embodiments include adding polymers to thicken nitroxide radioprotector containing liquid solutions. Any of the above described polymers can be used as a thickener for these formulations. For example, the following polymers can be used as thickening agents ethylene polymers, acrylic polymers, polyvinylpyrrolidones (PVPs), polyvinyl copolymers, cellulose polymers, natural polymers, polystyrene polymers, silicone polymers, inorganic polymers, and the like.

Those with skill in the art will readily know how to prepare thickened liquid solutions according to the methods described herein. Detail on how to prepare such liquids is provided in Remington's Pharmaceutical Sciences, 18$^{th}$ ed. 1990, which is hereby incorporated by reference in its entirety.

When the invention is practiced with a thickened liquid, it is advantageous to thicken the liquid to a viscosity of 20-100, 000 or more centipoise. In certain embodiments the formulations provided herein can have a viscosity between 400-2000 cps, or even more specific between 900-1500 cps. In more particular embodiments, the formulations can have a viscosity of approximately 1215 cps.

Methods of Using Compositions

Method embodiments include using any of the low-residue formulations described herein on a patient undergoing radiotherapy. In some embodiments the formulation can be applied shortly before radiotherapy. Suitable areas for applying the low-residue formulation include all areas of the skin and mucous membranes. Methods include, but are not limited to, applying formulations to the scalp, face, neck, chest, arms, legs, torso, back, and the like. Further methods include, but are not limited to, applying the formulations to mucous membranes, including but not limited to, areas of the mouth, nose, eyes, vagina, rectum and the like.

Some embodiments include rubbing a low-residue nitroxide radioprotector containing formulation onto an area of a patient undergoing radiotherapy. Rubbing can be accomplished using the practitioner's hands, typically gloved, or may alternatively be done with an applicator such as a cloth, towel, sponge, rag, gauze and the like. Other embodiments include spraying the low-residue formulation onto a treated area of a patient undergoing radiotherapy. Upon being sprayed on the treated area, the formulation may be left alone to absorb, or may be rubbed in to facilitate the absorption of the nitroxide radioprotector.

Further embodiments include topically applying a sufficient amount of a nitroxide radioprotector such as 4-hydroxy-2,2,6,6-tetramethylpiperidine-1-oxyl to prevent or treat harmful side effects caused by radiotherapy, wherein the 4-hydroxy-2,2,6,6-tetramethylpiperidine-1-oxyl is in solution and is in the form of a low-residue gel or thickened liquid.

In some embodiments, the formulations and methods described herein can be used to treat or prevent negative side effects of radiotherapy selected from skin conditions, mucous membrane conditions, and hair follicle conditions. In some embodiments the methods herein can be used to treat or prevent skin conditions including erythema, folliculitis, fibrosis, dry desquamation, moist desquamation, hyperpigmentation, dermatitis and the like. Additional embodiments include methods of treating mucous membrane conditions such as oral mucositis, proctitis, and the like. Further embodiments include methods of treating hair follicle conditions such as alopecia.

EXAMPLES

The following examples teach methods of making and using nitroxide radioprotector formulations. These examples are illustrative only and are not intended to limit the scope of the teachings herein.

Example I

Introduction

The following study was conducted to evaluate the in vitro percutaneous absorption of Tempol (4-hydroxy Tempo) from four vehicles using excised human skin from elective surgery. This study was conducted using procedures described in the FDA and AAPS Report of the Workshop on Principles and Practices of In Vitro Percutaneous Penetration Studies: Relevance to Bioavailability and Bioequivalence (*Pharm. Res.* 4:265, 1987), which is hereby incorporated by reference in its entirety.

Methods

The Tempol formulations used in this in vitro percutaneous absorption study were formulated by Dow Pharmaceutical Sciences, Petaluma, Calif. The composition of these formulations is summarized in Table 1.

TABLE 1

Tempol Formulation Composition

|  | Reference Ethanol Solution | Lightly Gelled Ethanol/ Water | Moderately Gelled Ethanol/ Water | Sprayable Ethanol/ Water |
|---|---|---|---|---|
|  | Formulation ID: | | | |
|  | I % by wt. | II % by wt. | III % by wt. | IV % by wt. |
| 4-Hydroxy tempo | 7 | 7 | 6.1 | 7 |
| Ethanol | 93 | 76.5 | 79.5 | 33 |
| Water | 0 | 15.5 | 13.1 | 56.87 |
| Klucel | 0 | 1 | 1.3 | 0 |
| Laponite XLG | 0 | 0 | 0 | 3.24 |
| Total: | 100 | 100 | 100 | 100.11 | pH of Formulations II, III, and IV were adjusted to 7-7.5 with citric acid

As indicated in Table 1, four Tempol containing formulations were prepared. Formulation I, was a reference ethanol solution, Formulation II was lightly gelled ethanol/water solution, Formulation I was a moderately gelled ethanol/water solution, and Formulation IV was a sprayable ethanol/water gel.

Franz static diffusion cells FDC-400 (15 mm diameter orifice, O-ring joint, Crown Bio Scientific, Clinton, N.J.) were mounted on 9-cell manifolds and maintained at a constant temperature of 32° C. by use of recirculating water baths. These cells had an opening with a nominal area of 1.767 $cm^2$ and a receptor compartment with a volume ranging between 12 to 14 mL. Each diffusion cell was assembled by placing the excised human abdominal skin from a single donor dermal-side down and then a Teflon® O-ring (which rested in the groove of the receptor side, bottom half, of the diffusion cell). The donor side, top half, of the diffusion cell was then placed on top of the O-ring which rested on the skin and was held in place by a pinch clamp. The joint between the donor and receptor compartments of each cell was wrapped with PARAFILM® to prevent evaporation of the receptor solution.

Each cell was then filled with receptor solution consisting of degassed PBS with 0.1% sodium azide and 1.5% Oleth-20. Air bubbles were dispelled from under the skin. The receptor fluid was continuously stirred using a Teflon magnetic stir bar and an inoculating loop cut to ~5.0 cm from the top of the loop. The skin was allowed to equilibrate with the receptor solution for 1 hour prior to application of formulation.

A finite dose (0.1 mL/$cm^2$) of each formulation was applied onto the skin using a syringe. Each formulation was applied in an alternating fashion to 6 diffusion cells at 0.18 mL of formulation per cell. The diffusion cell sampling port was sealed with PARAFILM® to prevent evaporation. Following the 15-minute exposure period, the entire contents of the receptor fluid was collected into a scintillation vial. The skin was wiped twice consecutively with a dry cotton swab, and cell caps were removed. Residual formulation was removed from the stratum corneum with multiple cellophane tape-strips until no more material was removed from the skin. The epidermis was physically separated from the dermis using tweezers. Each section of skin was placed into separate vials and labeled. All receptor, wipes, tape-strips, epidermis, and dermis samples were shipped to an analytical laboratory for analysis. Tempol content was reported as "Normal" and "Oxidized".

Results

Skin penetration of Tempol ranged from 0.003 to 0.01 percent of applied dose from the four formulations. The viable epidermis and dermis levels ranged from 0.2 to 2.8 percent of applied dose for the normal analysis and 1.1 to 6.6 percent of applied dose for the oxidized analysis. The moderately gelled ethanol/water formulation, Formulation III, exhibited the highest viable epidermis/dermis levels, 2.8% of applied dose for normal analysis and 6.6% applied dose for the oxidized analysis. The sprayable ethanol/water gel formulation, Formulation IV, obtained a result of 2.1% of applied dose for normal analysis. The reference ethanol solution, Formulation I, obtained a result of 4.4% of applied dose for the oxidized analysis. Skin deposition and penetration along with dose recovery are summarized in Tables 2 and 3. More specific results are provided in FIGS. 1-12.

TABLE 2

Percutaneous Absorption of Tempol (Normal and Oxidized)
Values are in % of Applied Dose

| Formulation | | Receptor Normal (%) | Wipes Normal (%) | TapeStrips Normal (%) | Viable E/D Normal (%) | Dose Recovered |
|---|---|---|---|---|---|---|
| I | mean | 0.01 | 15.02 | 0.27 | 1.52 | 16.82 |
| 7.00% tempol | SD | 0.005 | 8.02 | 0.05 | 1.05 | 8.25 |
| | % cv | 81.00 | 53.40 | 18.94 | 69.22 | 49.03 |
| II | mean | 0.003 | 25.17 | 0.29 | 0.20 | 25.66 |
| 6.98% tempol | SD | 0.004 | 10.11 | 0.10 | 0.18 | 10.25 |
| | % cv | 121.12 | 40.17 | 35.92 | 92.27 | 39.95 |
| III | mean | 0.01 | 35.16 | 0.28 | 2.81 | 38.25 |
| 6.09% tempol | SD | 0.01 | 6.55 | 0.15 | 1.96 | 6.49 |
| | % cv | 78.56 | 18.62 | 54.91 | 69.89 | 16.98 |
| IV | mean | 0.003 | 41.54 | 0.14 | 2.11 | 43.80 |
| 7.00% tempol | SD | 0.004 | 14.45 | 0.07 | 0.82 | 14.44 |
| | % cv | 110.22 | 34.79 | 48.66 | 39.11 | 32.97 |

| Formulation | | Receptor Oxidized (%) | Wipes Oxidized (%) | TapeStrips Oxidized (%) | Viable E/D Oxidized (%) | Dose Recovered |
|---|---|---|---|---|---|---|
| I | mean | 0.01 | 22.96 | 0.35 | 4.37 | 27.69 |
| 7.00% tempol | SD | 0.01 | 9.74 | 0.10 | 2.59 | 11.72 |
| | % cv | 91.52 | 42.43 | 28.14 | 59.23 | 42.33 |
| II | mean | 0.004 | 30.75 | 0.52 | 1.06 | 32.34 |
| 6.98% tempol | SD | 0.004 | 11.42 | 0.18 | 1.11 | 12.05 |
| | % cv | 111.15 | 37.13 | 35.54 | 104.64 | 37.27 |
| III | mean | 0.01 | 82.24 | 0.50 | 6.60 | 44.50 |
| 6.09% tempol | SD | 0.01 | 109.93 | 0.27 | 5.61 | 8.80 |
| | % cv | 78.70 | 133.68 | 55.03 | 85.04 | 19.78 |
| IV | mean | 0.004 | 45.95 | 0.26 | 3.34 | 49.54 |
| 7.00% tempol | SD | 0.004 | 14.49 | 0.12 | 1.05 | 14.54 |
| | % cv | 109.70 | 31.54 | 48.20 | 31.61 | 29.34 |

TABLE 3

Percutaneous Absorption of Tempol (Normal and Oxidized)
Values are in µg

| Formulation | | Receptor Normal (µg) | Wipes Normal (µg) | TapeStrips Normal (µg) | Viable E/D Normal (µg) | Cumm Amount (µg) | Tempol Amount (µg) | Dose Recovered |
|---|---|---|---|---|---|---|---|---|
| I | mean | 0.58 | 1511.36 | 27.30 | 153.62 | 1692.86 | 10094.00 | 16.82 |
| 7.00% tempol | SD | 0.47 | 788.38 | 5.34 | 106.56 | 809.35 | 100.76 | 8.25 |
| | % cv | 80.93 | 52.16 | 19.55 | 69.37 | 47.81 | 1.00 | 49.03 |
| II | mean | 0.32 | 2618.10 | 29.95 | 20.45 | 2668.82 | 10397.87 | 25.66 |
| 6.98% tempol | SD | 0.39 | 1062.63 | 10.64 | 18.89 | 1077.32 | 147.06 | 10.25 |
| | % cv | 121.02 | 40.59 | 35.54 | 92.37 | 40.37 | 1.41 | 39.95 |
| III | mean | 0.69 | 3213.88 | 25.12 | 256.44 | 3496.12 | 9125.87 | 38.25 |
| 6.09% tempol | SD | 0.54 | 622.82 | 13.58 | 178.77 | 623.95 | 239.04 | 6.49 |
| | % cv | 78.16 | 19.38 | 54.08 | 69.71 | 17.85 | 2.62 | 16.98 |
| IV | mean | 0.39 | 4889.76 | 16.68 | 248.48 | 5155.32 | 11763.50 | 43.80 |
| 7.00% tempol | SD | 0.43 | 1702.51 | 8.03 | 98.89 | 1702.76 | 200.73 | 14.44 |
| | % cv | 110.15 | 34.82 | 48.13 | 39.80 | 33.03 | 1.71 | 32.97 |

| Formulation | | Receptor Oxidized (µg) | Wipes Oxidized (µg) | TapeStrips Oxidized (µg) | Viable E/D Oxidized (µg) | Cumm Amount (µg) | Tempol Amount (µg) | Dose Recovered |
|---|---|---|---|---|---|---|---|---|
| I | mean | 0.73 | 2312.23 | 35.43 | 439.36 | 2787.75 | 10094.00 | 27.69 |
| 7.00% tempol | SD | 0.66 | 964.49 | 10.22 | 257.30 | 1158.30 | 100.76 | 11.72 |
| | % cv | 91.56 | 41.71 | 28.85 | 58.56 | 41.55 | 1.00 | 42.33 |
| II | mean | 0.39 | 3196.10 | 54.03 | 110.24 | 3360.77 | 10397.87 | 32.34 |
| 6.98% tempol | SD | 0.44 | 1191.31 | 19.00 | 115.65 | 1257.47 | 147.06 | 12.05 |
| | % cv | 111.16 | 37.27 | 35.17 | 104.91 | 37.42 | 1.41 | 37.27 |
| III | mean | 0.78 | 7359.87 | 45.10 | 606.41 | 8012.16 | 9125.87 | 89.34 |
| 6.09% tempol | SD | 0.61 | 9631.31 | 24.44 | 528.16 | 9637.88 | 239.04 | 110.11 |
| | % cv | 78.53 | 130.86 | 54.20 | 87.10 | 120.29 | 2.62 | 123.25 |

TABLE 3-continued

Percutaneous Absorption of Tempol (Normal and Oxidized)
Values are in μg

| | | | | | | | | |
|---|---|---|---|---|---|---|---|---|
| IV | mean | 0.45 | 5409.74 | 30.07 | 392.67 | 5832.94 | 11763.50 | 49.54 |
| 7.00% tempol | SD | 0.50 | 1722.82 | 14.33 | 126.28 | 1729.43 | 200.73 | 14.54 |
| | % cv | 109.61 | 31.85 | 47.68 | 32.16 | 29.65 | 1.71 | 29.34 |

Conclusion

The percentage of the applied dose and amount of Tempol penetrating the skin into the receptor fluid was very low and ranged from 0.003% to 0.01% and 0.32 ug/1.77 cm$^2$ to 0.78 ug/1.77 cm$^2$ of skin respectively, following a 15 minute duration of skin exposure. This study shows that the moderately gelled ethanol/water formulation, Formulation III, achieved higher skin (epidermis/dermis) levels (2.8% of applied dose for normal analysis and 6.6% applied dose for the oxidized analysis) of Tempol but not higher skin penetration compared to the reference ethanol formulation, Formulation I. Results from this initial study suggest that Formulation III would achieve comparable or better clinical efficacy following topical application to the head. In addition, Formulation III should have better formulation retention to the skin (low run-off) compared to Formulation I.

Example II

Introduction

This study evaluated the effect of multiple applications of a moderately gelled 7% Tempol ethanol/water formulation (Formulation V) on the in vitro percutaneous absorption of Tempol using similar test procedures as employed in Example I. These test procedures were consistent with the FDA and AAPS Report of the Workshop on Principles and Practices of In Vitro Percutaneous Penetration Studies: Relevance to Bioavailability and Bioequivalence (*Pharm. Res.* 4:265, 1987), which is hereby incorporated by reference in its entirety.

Test formulations used in this in vitro percutaneous absorption study were prepared by Dow Pharmaceutical Sciences, Petaluma, Calif. Formulation compositions are summarized in Table 4 The viscosity of Formulation V was measured using a Brookfield RVDV-1+ viscometer. A sample weighing 8.4134 grams had a measured viscosity of 1215 cps at 22.9° C.

TABLE 4

Tempol Formulation Composition

| | Tempol Formulation | Vehicle Formulation | |
|---|---|---|---|
| | Formulation ID: | | |
| | Formulation V % by wt. | Formulation VI % by wt. | Supplier |
| 4-Hydroxy Tempo | 7 | 0 | Mitos |
| Ethanol | 79.0 | 86.0 | Spectrum |
| Water | 13.0 | 13.0 | McGaw |
| Klucel | 1.0 | 1.0 | Hercules |
| Total: | 100 | 100 | |

Each of the four application regimens were performed on six cells: (1) a single application of Tempol formulation (Formulation V) 2) two applications of Tempol formulation (Formulation V), (3) three applications of Tempol formulation (Formulation V), and (4) one application of Tempol formulation (Formulation V) followed by one application of Vehicle formulation (Formulation VI). Each application of formulation had a 30 minute duration of exposure to the skin surface.

The skin was wiped with two dry cotton swabs after each application. Upon completion of the final application and skin wiping, the stratum corneum was removed from the skin. All samples of stratum corneum along with the remaining skin (viable epidermis/dermis), receptor fluid, and skin surface wipes collected during the study were analyzed in a laboratory for Tempol content. Tempol content was reported as "Normal", "Oxidized", and "Reduced."

Methods

Franz static diffusion cells (15 mm diameter orifice, O-ring joint, Crown Bio Scientific, Clinton, N.J.) were mounted on 9-cell manifolds and maintained at a constant temperature of 32° C. by use of re-circulating water baths. These cells had an opening with a nominal area of 1.77 cm$^2$ and a receptor compartment with a volume ranging between 12 to 14 mL. Each diffusion cell was assembled by placing the excised human abdominal skin from a single donor dermal-side down and then a Teflon® O-ring (which rested in the groove of the donor side, top half, of the diffusion cell. The donor side (top half) of the diffusion cell was then placed on top of the O-ring resting on the skin and held in place by use of a pinch clamp. The joint between the donor and receptor compartments of each cell was wrapped with Parafilm® to prevent evaporation of the receptor solution.

Each cell was then filled with receptor solution consisting of degassed PBS with 0.1% sodium azide and 1.5% Oleth-20. Air bubbles were dispelled from under the skin. The receptor fluid was continuously stirred using a Teflon magnetic stir bar and an inoculating loop cut to ~3.0 cm from the top of the loop. The skin was allowed to equilibrate with the receptor solution for 1 hour prior to the application of formulation.

A finite dose (0.1 mL/cm$^2$) of formulation was applied on to the skin using a displacement pipette. The formulation was applied in an alternating fashion to 6 diffusion cells at 0.18 mL of formulation per cell. The diffusion cell sampling port was sealed with PARAFILM® to prevent evaporation. Following the 30-minute exposure period, the entire contents of the receptor fluid were collected into a scintillation vial. If appropriate, the cell was re-dosed with test formulation after removal of the previous dose using two cotton swabs wiped across the skin surface. After exposure to the last application of test formulation, the skin was wiped twice consecutively with a dry cotton swab. Cell caps were removed. Residual formulation was removed from the stratum corneum with multiple cellophane tape-strips until no more material was removed from the skin. The remaining viable epidermis/dermis was collected. All receptor, wipes, tape-strips, and viable epidermis/dermis samples were shipped to an analytical laboratory for analysis.

Results

Data was provided from the analytical lab in the form of normal and oxidized Tempol concentrations. Since reduced Tempol is not detectable by the analytical method, Tempol in the samples was oxidized such that all Tempol present was in the oxidized form. Oxidized Tempol represents the total amount of Tempol recovered. Reduced Tempol was calculated as the oxidized Tempol minus the normal Tempol.

Skin penetration of reduced Tempol ranged from 0 µg/1.77 cm$^2$ to 0.62 µg/1.77 cm$^2$ of skin following a 30 minute duration of skin exposure. The second application of Tempol and additional 30 minute exposure to the skin surface resulted in a cumulative range from 2.94 µg/1.77 cm$^2$ to 3.80 µg/1.77 cm$^2$ of skin. Application of the vehicle formulation (Formulation VI) following a dose of Tempol formulation (Formulation V) did not increase the amount of reduced Tempol penetrating the skin. The third application of Tempol and additional 30 minute exposure to the skin surface resulted in a cumulative amount of 8.8 µg reduced Tempol/1.77 cm$^2$ of skin.

Figure 13:
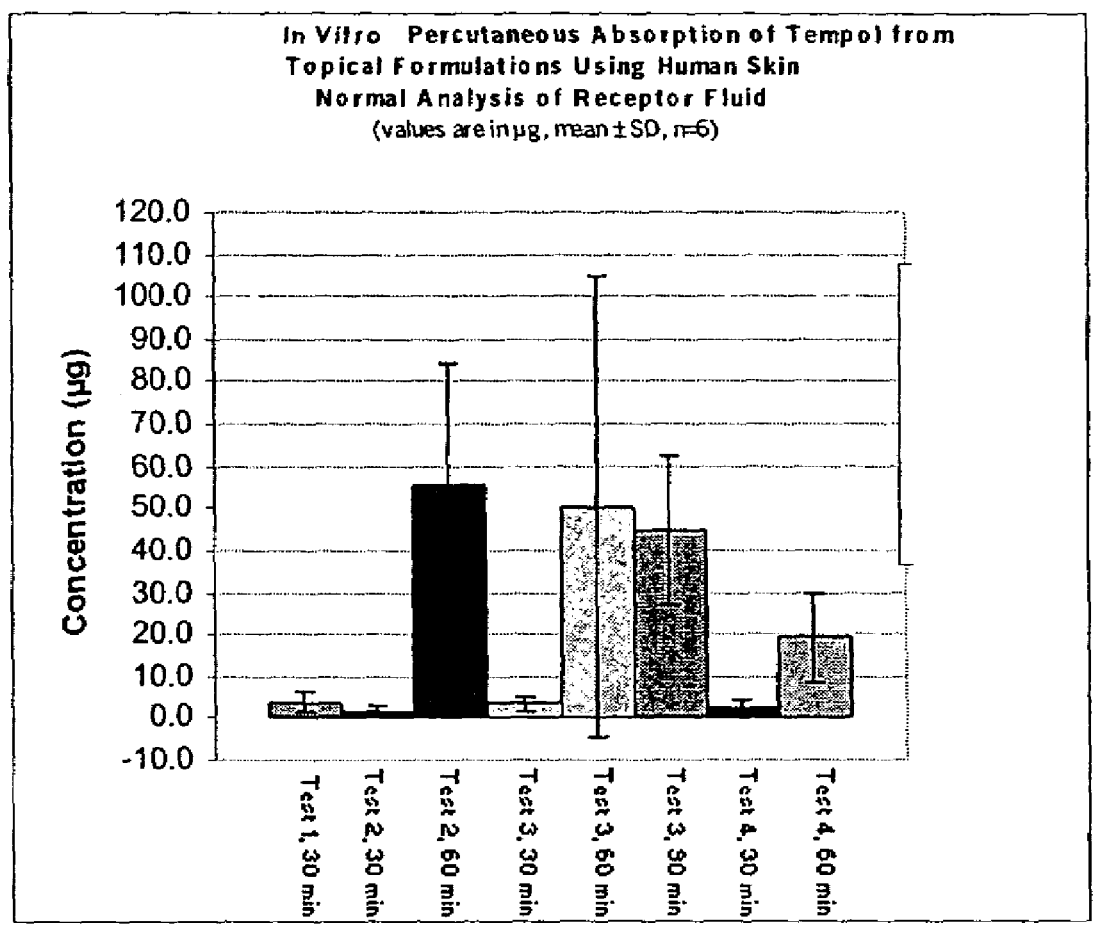
FIG. 13 is a bar graph providing the measured concentration of normal Tempol in receptor fluid after in vitro percutaneous absorption of a moderately gelled 7% Tempol ethanol/water topical formulation into human skin for 15 minutes.
Figure 14:
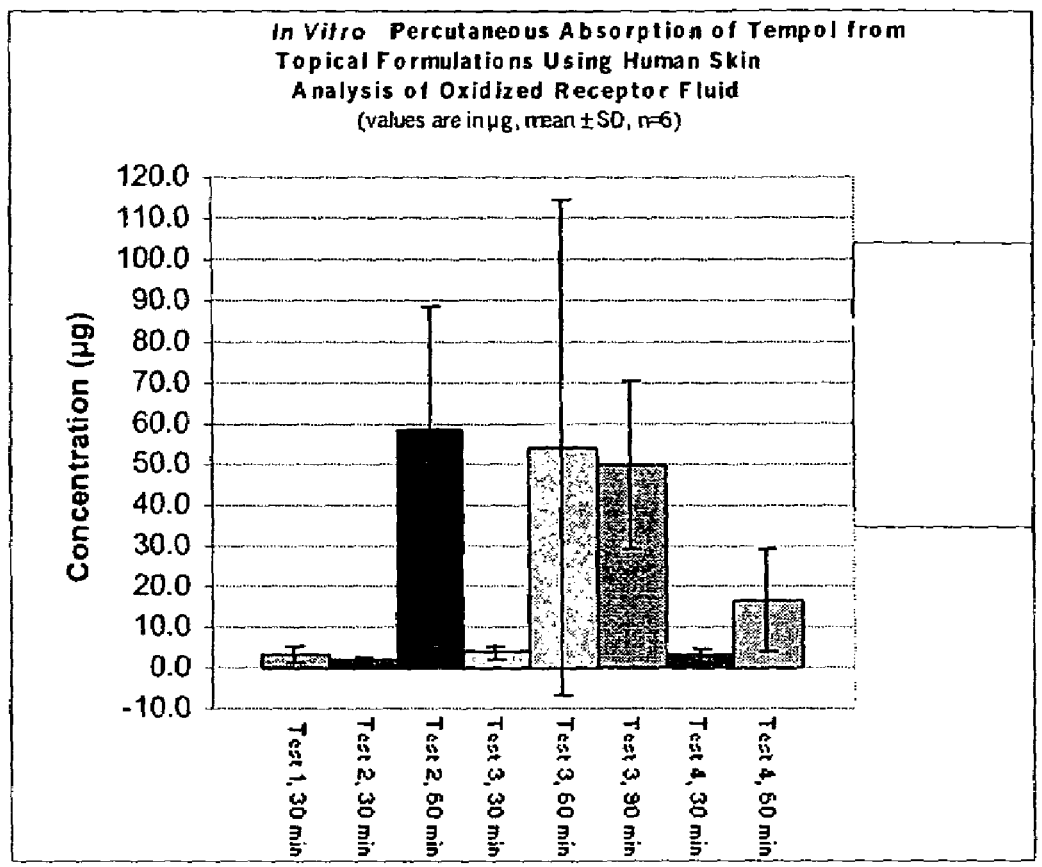
FIG. 14 is a bar graph providing the measured concentration of oxidized Tempol in receptor fluid after in vitro percutaneous absorption of a moderately gelled 7% Tempol ethanol/water topical formulation into human skin for 15 minutes.

The viable epidermis and dermis levels ranged from 153.7 µg/1.77 cm$^2$ to 496.5 µg/1.77 cm$^2$ for the normal analysis, 248.0 µg/1.77 cm$^2$ to 595.5 µg/1.77 cm$^2$ for the oxidized analysis, and 57.3 µg/1.77 cm$^2$ to 96.9 µg/1.77 cm$^2$ for the reduced result. The highest viable epidermis/dermis levels were seen with two applications of Tempol, 184.1 µg reduced Tempol/1.77 cm$^2$ of skin. Skin penetration and deposition are summarized in Tables 5(a and b) and 6(a and b). Other results are provided in FIGS. 13 and 14.

Tables 5a & 5b: Percutaneous Absorption of Tempol in µg

TABLE 5a

Intact Values are in µg, n = 6 cells

| Test | | Viable Normal | Viable Oxidized | Viable Reduced |
|---|---|---|---|---|
| 1 | mea | 156. | 253. | 96.9 |
| Single | SD | 84.6 | 113. | 44.0 |
| Form. V | % | 54.2 | 44.8 | 45.4 |
| 2 | mea[1] | 479. | 663. | 184. |
| Two applications | SD[1] | 232. | 345. | 167. |
| Form. V | % | 48.5 | 52.1 | 91.2 |
| 3 | mea | 425. | 595. | 170. |
| Three | SD | 180. | 310. | 130. |
| Form. V | % | 42.5 | 52.2 | 76.8 |
| 4 | mea | 153. | 248. | 94.3 |
| Form. V then | SD | 90.6 | 141. | 58.0 |
| Form. VI | % | 58.9 | 57.2 | 61.5 |

[1]Test 2.

TABLE 5b

Normal Values are in µg,

| Test | | 30 minutes Normal (µg) | 60 minutes Normal (µg) | 90 minutes Normal (µg) |
|---|---|---|---|---|
| 1 | mea | 3.97 | n/a | n/a |
| Single | SD | 2.25 | n/a | n/a |
| Form. V | % | 56.7 | n/a | n/a |
| 2 | mea | 1.93 | 57.7 | n/a |
| Two applications | SD | 1.11 | 29.4 | n/a |
| Form. V | % | 57.2 | 50.8 | n/a |
| 3 | mea | 3.48 | 53.8 | 98.7 |
| Three | SD | 1.65 | 55.9 | 56.1 |
| Form. V | % | 47.4 | 103.9 | 56.8 |
| 4 | mea | 2.41 | 21.5 | n/a |
| Form. V then | SD | 1.88 | 12.5 | n/a |
| Form. VI | % | 78.1 | 58.1 | n/a |

Tables 6a & 6b.

Percutaneous Absorption of Tempol in µg

TABLE 6a

Oxidized Values are in µg,

| Test | | 30 minutes Oxidized (µg) | 60 minutes Oxidized (µg) | 90 minutes Oxidized (µg) |
|---|---|---|---|---|
| 1 | mea | 3.55 | n/a | n/a |
| Single | SD | 1.95 | n/a | n/a |
| Form. V | % | 54.9 | n/a | n/a |
| 2 | mea | 1.96 | 60.7 | n/a |
| Two applications | SD | 0.86 | 30.6 | n/a |
| Form. V | % | 43.6 | 50.3 | n/a |
| 3 | mea | 3.71 | 57.6 | 107.5 |
| Three | SD | 1.51 | 61.6 | 61.9 |
| Form. V | % | 40.6 | 106.9 | 57.5 |
| 4 | mea | 3.03 | 19.6 | n/a |
| Form. V then | SD | 1.53 | 13.8 | n/a |
| Form. VI | % | 50.5 | 70.4 | n/a |

TABLE 6b

Reduced Values are in µg,

| Test | | 30 minutes Reduced (µg) | 60 minutes Reduced (µg) | 90 minutes Reduced (µg) |
|---|---|---|---|---|
| 1 | mea | — | n/a | n/a |
| Single | SD | 0.42 | n/a | n/a |
| Form. V | % | — | n/a | n/a |
| 2 | mea | 0.03 | 2.94 | n/a |
| Two applications | SD | 0.42 | 1.41 | n/a |
| Form. V | % | 1424. | 47.9 | n/a |
| 3 | mea | 0.24 | 3.80 | 8.80 |
| Three | SD | 0.25 | 5.96 | 6.05 |
| Form. V | % | 106.5 | 156.7 | 68.7 |
| 4 | mea | 0.62 | — | n/a |
| Form. V then | SD | 0.87 | 10.0 | n/a |
| Form. VI | % | 139.1 | — | n/a |

Drug deposition and penetration was statistically evaluated by performing unpaired t-tests (significant differences between formulations are defined with a value of $p<0.05$). After 30 minute duration of skin exposure, the four application regimens are statistically comparable to each other in penetration for the oxidized and normal Tempol ($p<0.05$) with the exception the oxidized Tempol for Test 2 versus Test 3 ($p=0.033$). The amount of normal, oxidized, and reduced Tempol in Test 2 was statistically comparable to Test 3 after the second application of Tempol and additional 30 minute duration of skin exposure. Test 2 after the second application of Tempol was significantly higher than Test 4 after the application of vehicle and additional 30 minute duration of skin exposure for the normal and oxidized analysis. Test 2, 3, and 4 produced comparable levels of reduced Tempol after the second dosing and additional time. The third application results from test 3 produced levels that were twice as high as the levels in the second time point. This is suggestive of Tempol reaching a steady state of absorption.

Skin deposition of normal and oxidized Tempol after multiple applications (test 2 and 3) was significantly higher ($p<0.05$) than a single application (test 1 and 4). Reduced Tempol was statistically comparable between all four application tests. In test 4, application of the vehicle did provide a washing-in effect, increasing the levels of normal and oxidized Tempol, but it was not as great of an effect as multiple applications of the active formulation.

Conclusion

This study shows that two sequential applications of the moderately gelled ethanol/water formulation achieved higher deposition and penetration levels of Tempol than a single application.

Example 3

Prophylactic Treatment for Brain Tumor

The moderately gelled 7% Tempol ethanol/water formulation of Example II (Formulation V) is applied twice to the scalp of a brain tumor patient prior to radiation treatment, and the solvent is allowed to evaporate. Each application of the formulation has a 30 minute duration of exposure to the scalp. Conventional radiation therapy is then administered to the tumor through the scalp. Following treatment, the patient does not experience epidermal burning, and hair loss that would otherwise result within 1-2 weeks.

Although the teachings herein have been described with reference to embodiments and examples, it should be understood that various modifications can be made without departing from the spirit of the invention. Accordingly, the teachings herein are limited only by the following claims. All references cited herein are hereby expressly incorporated by reference in their entireties.

What is claimed is:

1. A pharmaceutical composition for use in ameliorating an effect of radiotherapy on skin, mucous membranes, or hair follicles comprising:
a solvent; and
an effective prophylactic or therapeutic amount of a nitroxide radioprotector in solution in the solvent, wherein the pharmaceutical composition is in the form of a low-residue gel.

2. The pharmaceutical composition of claim 1, wherein the nitroxide radioprotector is 4-hydroxy-2,2,6,6-tetramethylpiperidine-1-oxyl.

3. The pharmaceutical composition of claim 1, wherein the solvent is selected from the group consisting of water, urea, alcohols, and glycols.

4. The pharmaceutical composition of claim 3, wherein the solvent is an alcohol selected from the group consisting of methanol, ethanol, propanol, and butanol.

5. The pharmaceutical composition of claim 3, wherein the glycol is selected from the group consisting of ethylene glycol and propylene glycol.

6. The pharmaceutical composition of claim 1, wherein the effect of radiotherapy is selected from the group consisting of skin conditions, mucous membrane conditions, hair follicle conditions, cytotoxicity, and polynucleic acid damage.

7. The pharmaceutical composition of claim 6, wherein the skin condition is selected from erythema, folliculitis, fibrosis, dry desquamation, moist desquamation, hyperpigmentation, and dermatitis.

8. The pharmaceutical composition of claim 6, wherein the mucous membrane condition is selected from oral mucositis and proctitis.

9. The pharmaceutical composition of claim 6, wherein the hair follicle condition is alopecia.

10. The pharmaceutical composition of claim 1, wherein the effective prophylactic or therapeutic amount of a nitroxide radioprotector is an amount from about 0.01 to about 100 mg/ml of the total composition.

11. The pharmaceutical composition of claim 1, further comprising a polymer selected from the group consisting from ethylene polymers, acrylic polymers, polyvinylpyrrolidones (PVPs), polyvinyl copolymers, cellulose polymers, natural polymers, polystyrene polymers, silicone polymers, and inorganic polymers.

12. The pharmaceutical composition of claim 1, having a viscosity such that the nitroxide radioprotector will remain in contact with a treated area for a sufficient period of time to allow absorption of a pharmacologically effective amount into said treated area.

13. A pharmaceutical composition for use in ameliorating an effect of radiotherapy to skin or mucous membranes, comprising:
a solvent; and
an effective prophylactic or therapeutic amount of a nitroxide radioprotector in solution in the solvent, wherein the pharmaceutical composition is in the form of a low-residue gel or thickened liquid that does not leave an amount of residue sufficient to enhance burning to the skin or mucous membranes when radiotherapy is applied.

14. The pharmaceutical composition of claim 13, wherein the nitroxide radioprotector is 4-hydroxy-2,2,6,6-tetramethylpiperidine-1-oxyl.

15. A pharmaceutical composition for use in preventing or treating alopecia comprising:
a solvent; and
an effective prophylactic or therapeutic amount of 4-hydroxy-2,2,6,6-tetramethylpiperidine-1-oxyl in solution in the solvent, wherein the pharmaceutical composition is in the form of a low-residue gel.

16. A method of treating a patient, comprising topically applying a sufficient amount of a nitroxide radioprotector to prevent or treat harmful side effects caused by radiotherapy, wherein the nitroxide radioprotector is in solution in a solvent and the solution is in the form of a low-residue gel or a low-residue thickened liquid.

17. The method of claim 16 wherein the nitroxide radioprotector is 4-hydroxy-2,2,6,6-tetramethylpiperidine-1-oxyl.

18. The method of claim 16, wherein the solvent is selected from the group consisting of water, urea, alcohols, and glycols.

19. The method of claim 16 where the harmful side effect is selected from the group consisting of skin conditions, mucous membrane conditions, hair follicle conditions, cytotoxicity and polynucleic acid damage.

20. The method of claim 19 wherein, the skin condition is selected from erythema, folliculitis, fibrosis, dry desquamation, moist desquamation, hyperpigmentation, and dermatitis.

21. The method of claim 19 wherein, the mucous membrane condition is selected from oral mucositis and proctitis.

22. The method of claim 19, wherein the hair follicle condition is alopecia.

23. A method of treating a patient, comprising:
topically applying a sufficient amount of a nitroxide radioprotector to prevent or treat a harmful side effect caused by radiotherapy, wherein the nitroxide radioprotector is in solution in solvent, has a sufficient viscosity such that it is retained in place on the patient, and the solution is in the form of a low-residue gel or a low-residue thickened liquid; and
applying radiotherapy to said patient.

* * * * *

UNITED STATES PATENT AND TRADEMARK OFFICE
CERTIFICATE OF CORRECTION

PATENT NO. : 7,625,928 B2 Page 1 of 1
APPLICATION NO. : 10/675225
DATED : December 1, 2009
INVENTOR(S) : Maxwell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1081 days.

Signed and Sealed this

Second Day of November, 2010

David J. Kappos
*Director of the United States Patent and Trademark Office*